United States Patent
Stankovic et al.

(10) Patent No.: US 9,371,528 B2
(45) Date of Patent: Jun. 21, 2016

(54) METHODS FOR TREATING POLYPS

(71) Applicant: Massachusetts Eye and Ear Infirmary, Boston, MA (US)

(72) Inventors: Konstantina M. Stankovic, Boston, MA (US); Ralph Metson, Newton, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 14/179,510

(22) Filed: Feb. 12, 2014

(65) Prior Publication Data

US 2014/0255421 A1 Sep. 11, 2014

Related U.S. Application Data

(63) Continuation of application No. 12/863,415, filed as application No. PCT/US2009/031349 on Jan. 16, 2009, now abandoned.

(60) Provisional application No. 61/011,568, filed on Jan. 18, 2008.

(51) Int. Cl.
| | | |
|---|---|---|
| *A61K 31/41* | (2006.01) | |
| *A61K 31/405* | (2006.01) | |
| *C12N 15/113* | (2010.01) | |
| *C12Q 1/68* | (2006.01) | |
| *C07K 14/00* | (2006.01) | |
| *C07K 16/40* | (2006.01) | |

(52) U.S. Cl.
CPC ............ *C12N 15/1135* (2013.01); *A61K 31/41* (2013.01); *C07K 14/00* (2013.01); *C07K 16/40* (2013.01); *C12N 15/1137* (2013.01); *C12Q 1/6883* (2013.01); *C12Q 2600/158* (2013.01)

(58) Field of Classification Search
CPC .... A61K 31/40; A61K 31/4035; A61K 31/41
USPC ................................. 514/381, 415
See application file for complete search history.

(56) References Cited

U.S. PATENT DOCUMENTS

| 5,883,116 | A | 3/1999 | Tang et al. |
|---|---|---|---|
| 2006/0178364 | A1 | 8/2006 | Jung et al. |
| 2011/0104166 | A1 | 5/2011 | Stankovic et al. |

FOREIGN PATENT DOCUMENTS

| EP | 0450813 A2 | 10/1991 |
|---|---|---|
| WO | WO-9924037 A1 | 5/1999 |
| WO | WO-0038676 A1 | 7/2000 |
| WO | WO-2005019471 A2 | 3/2005 |
| WO | WO-2009092052 A2 | 7/2009 |

OTHER PUBLICATIONS

Alberts et al. (1994) "Expression of a Peptide Inhibitor of Protein Phosphatase 1 Increases Phosphorylation and Activity of CREB in NIH 3T3 Fibroblasts," Molecular and Cellular Biology 14(7):4398-4407.

Allen et al. (1997) "Spinophilin, a novel protein phosphatase 1 binding protein localized to dendritic spines," Proc. Natl. Acad. Sci. USA 94:9956-9961.

Anand et al. (2006) "Inflammatory pathway gene expression in chronic rhinosinusitis," Am. J. Rhinol. 20:471-476.

Araki et al. (1988) "Complete amino acid sequence of human plasma Zn-$\alpha_2$-glycoprotein and its homology to histocompatibility antigens," Proc. Natl. Acad. Sci. USA 85:679-683.

Armstrong et al. (1997) "PPP1R6, a novel member of the family of glycogen-targetting subunits of protein phosphatase 1," FEBS Letters 418:210-214.

Bahram et al. (1994) "A second lineage of mammalian major histocompatibility complex class I genes," Proc. Natl. Acad. Sci. USA 91: 6259-6263.

Bao et al. (2004) "Periostin potently promotes metastatic growth of colon cancer by augmenting cell survival via the Akt/PKB pathway," Cancer Cell 5:329-339.

Bao et al. (2005) "Zinc-$\alpha_2$-glycoprotein, a lipid mobilizing factor, is expressed and secreted by human (SGBS) adipocytes," FEBS Letters 579:41-47.

Bardelli et al. (1999) "A Peptide Representing the Carboxyl-terminal Tail of the Met Receptor Inhibits Kinase Activity and Invasive Growth," The Journal of Biological Chemistry 274(41):29274-29281.

Baril et al. (2007) "Periostin promotes invasiveness and resistance of pancreatic cancer cells to hypoxia-induced cell death: role of the $\beta_4$ integrin and the Pl3k pathway," Oncogene 26:2082-2094

Barker et al. (1993) "Sequence of human protein serine/threonine phosphatase 1 gamma and localization of the gene (PPP1CC) encoding it to chromosome bands 12q24.1-q24.2," Biochimica et Biophysica Acta, 1178:228-233.

Barker et al. (1994) "Three genes for protein phosphatase 1 map to different human chromosomes: sequence, expression and gene localisation of protein serine/threonine phosphatase 1 beta (PPP1CB)," Biochimica et Biophysica Acta, 1220:212-218.

Bateman et al. (2003) "Nasal polyps: Still more questions than answers," The Journal of Laryngology & Otology 117:1-9.

Benson et al. (2004) "Gene profiling reveals increased expression of uteroglobin and other anti-inflammatory genes in glucocorticoid-treated nasal polyps," J. Allergy Clin. Immunol. 113:1137-1143.

Bing et al. (2004) "Zinc-α2-glycoprotein, a lipid mobilizing factor, is expressed in adipocytes and is up-regulated in mice with cancer cachexia," Proc. Natl. Acad. Sci. USA 101(8):2500-2505.

Blais et al. (1996) "Interleukin-4 and interleukin-13 inhibit estrogen-induced breast cancer cell proliferation and stimulate GCDFP-15 expression in human breast cancer cells," Molecular and Cellular Endocrinology 121:11-18.

(Continued)

*Primary Examiner* — Kevin E Weddington
(74) *Attorney, Agent, or Firm* — Goodwin Procter LLP

(57) ABSTRACT

The invention relates generally to methods and compositions for treating sinusitis, asthma, or polyps. The invention also relates to methods and compositions for treating nasal polyps.

14 Claims, 6 Drawing Sheets

(56) References Cited

OTHER PUBLICATIONS

Bolger et al. (2007) "Gene expression analysis in sinonasal polyposis before and after oral corticosteroids: A preliminary investigation," Otolaryngology—Head and Neck Surgery 137:27-33.
Bottaro et al. (1991) "Identification of the Hepatocyte Growth Factor Receptor as the c-*met* Proto-Oncogene Product," Science 251:802-804.
Bresciani et al. (2001) "Rhinosinusitis in severe asthma," J. Allergy Clin. Immunol. 107(1):73-80.
Brockdorff et al. (1997) "Interleukin 2 induces a transient downregulation of protein phosphatase 1 and 2A activity in human T cells," Tissue Antigens 49:228-235.
Cao et al. (2001) "Neutralizing monoclonal antibodies to hepatocyte growth factor/scatter factor (HGF/SF) display antitumor activity in animal models," PNAS 98(13):7443-7448.
Cohen (2002) "Protein phosphatase 1—targeted in many directions," Journal of Cell Science 115(2):241-256.
Colbran et al. (2003) "Analysis of Specific Interactions of Native Protein Phosphatase 1 Isoforms with Targeting Subunits," Methods in Enzymology 366:156-175.
Colilla et al. (2003) "Evidence for gene-environment interactions in a linkage study of asthma and smoking exposure," J. Allergy Clin. Immunol. 111:840-846.
Colombo et al. (2007) "Hepatocyte Growth Factor/Scatter Factor Promotes Retinal Angiogenesis through Increased Urokinase Expression," Investigative Ophthalmology & Visual Science 48(4):1793-1800.
Dejardin et al. (1991) "Stimulatory effect of oestradiol-17β and tamoxifen on gross cystic disease fluid protein 15 000 production and mRNA levels in T47D human breast cancer cells," Journal of Molecular Endocrinology 7:105-112.
Descazeaud et al. (2006) "Characterization of ZAG Protein Expression in Prostate Cancer Using a Semi-Automated Microscope System," The Prostate 66:1037-1043.
Figueiredo et al. (2007) "Microarray cDNA to identify inflammatory genes in nasal polyposis," American Journal of Rhinology 21(2):231-235.
Fritz et al. (2003) "Nasal mucosal gene expression in patients with allergic rhinitis with and without nasal polyps," J. Allergy Clin. Immunol. 112(6):1057-1063.
Gaubin et al. (1999) "Potent Inhibition of CD4/TCR-Mediated T Cell Apoptosis by a CD4-Binding Glycoprotein Secreted from Breast Tumor and Seminal Vesicle Cells," The Journal of Immunology 162:2631-2638.
Gillen et al. (2002) "Periostin Secreted by Epithelial Ovarian Carcinoma Is a Ligand for $α_vβ_3$ and $α_vβ_5$ Integrins and Promotes Cell Motility," Cancer Research 62:5358-5364.
Gliklich and Metson (1994) "A Comparison of Sinus Computed Tomography (CT) Staging Systems for Outcomes Research," Am. J. Rhinology, 8(6):291-297.
Guajardo et al. (2005) "Altered gene expression profiles in nasal respiratory epithelium reflect stable versus acute childhood asthma," J. Allergy Clin. Immunol. 115(2):243-251.
Guerin et al. (2000) "Glioma Inhibition by HGF/NK2, an Antagonist of Scatter Factor/Hepatocyte Growth Factor," Biochemical and Biophysical Research Communications 273(1):287-293.
Haagensen et al. (1990) "Review of GCDFP-15. An Apocrine Marker Protein," Annals New York Academy of Sciences 586:161-173.
He et al. (2001) "Zinc-α2-Glycoprotein Hinders Cell Proliferation and Reduces *cdc*2 Expression," Journal of Cellular Biochemistry Supplement 36:162-169.
Hillier et al. (2003) "The DNA sequence of human chromosome 7," Nature 424:157-164.
International Preliminary Report on Patentability for PCT/US2009/031349 mailed Jul. 20, 2010 (9 pages).
International Search Report for PCT/US2009/031349 mailed Aug. 19, 2009 (8 pages).
Jagadeeswaran et al. (2006) "Functional Analysis of c-Met/Hepatocyte Growth Factor Pathway in Malignant Pleural Mesothelioma," Cancer Res. 66(1):352-361.
Kim et al. (2007) "Polony Multiplex Analysis of Gene Expression (PMAGE) in Mouse Hypertrophic Cardiomyopathy," Science 316:1481-1484.
Kitano et al. (2006) "Origin and evolution of gene for prolactin-induced protein," Gene 383:64-70.
Koppelman (2001), "Genetics of asthma and atopy," Dissertation, Rijksuniversiteit Groningen, 1-25.
Krouse et al. (2007) "Executive summary: Asthma and the unified airway," Otolaryngology—Head & Neck Surgery 136:699-706.
Iekushi et al. (2007) "Novel Mechanisms of Valsartan on the Treatment of Acute Myocardial Infarction Through Inhibition of the Antiadhesion Molecule Periostin," Hypertension 49:1409-1414.
Liu et al. (2002) "KEPI, a PKC-dependent Protein Phosphatase 1 Inhibitor Regulated by Morphine," The Journal of Biological Chemistry 277(15):13312-13320.
Liu et al. (2004) "Gene expression profiles in human nasal polyp tissues studied by means of DNA microarray," J. Allergy Clin. Immunol. 114(4):783-790.
Maulik et al. (2002) "Modulation of the c-Met/Hepatocyte Growth Factor Pathway in Small Cell Lung Cancer," Clinical Cancer Research 8:620-627.
Munton et al. (2004) "The role of protein phosphatase-1 in the modulation of synaptic and structural plasticity," FEBS Letters 567:121-128.
Murphy et al. (1987) "Isolation and Sequencing of a cDNA Clone for a Prolactin-inducible Protein (PIP)," The Journal of Biological Chemistry 262(31):15236-15241.
Norris et al. (2007) "Periostin Regulates Collagen Fibrillogenesis and the Biomechanical Properties of Connective Tissues," Journal of Cellular Biochemistry 101:695-711.
Ober (2005) "*HLA-G*: An Asthma Gene on Chromosome 6p," Immunol. Allergy Clin. N. Am. 25:669-679.
Orlandi et al. (2007) "Microarray analysis of allergic fungal sinusitis and eosinophilic mucin rhinosinusitis," Otolaryngology-Head and Neck Surgery 136(5):707-713.
Pott et al. (2003) "The preferential β3-adrenoceptor agonist BRL 37344 increases force via β1-/β2-adrenoceptors and induces endothelial nitric oxide synthase via β3-adrenoceptors in human atrial myocardium," British Journal of Pharmacology 138:521-529.
Rho et al. (2006) "Overexpression of Hepatocyte Growth Factor and Its Receptor c-Met in Nasal Polyps," Arch. Otolaryngol. Head Neck Surg. 132:985-989.
Rolli et al. (2007) "Lipolysis is altered in MHC class I zinc-$α_2$-glycoprotein deficient mice," FEBS Letters 581:394-400.
Sarrouilhe et al. (2006) "Spinophilin: from partners to functions," Biochimie 88:1099-1113.
Satoh et al. (1998) "Neurabin-II/Spinophilin. An Actin Filament-Binding Protein With One PDZ Domain Localized at Cadherin-Based Cell-Cell Adhesion Sites," The Journal of Biological Chemistry 273(6):3470-3475.
Sattler and Salgia (2007) "c-Met and Hepatocyte Growth Factor: Potential as Novel Targets in Cancer Therapy," Current Oncology Reports 9:102-108.
Shao et al. (2004) "Acquired Expression of Periostin by Human Breast Cancers Promotes Tumor Angiogenesis through Up-Regulation of Vascular Endothelial Growth Factor Receptor 2 Expression," Molecular and Cellular Biology 24(9):3992-4003.
Song et al. (1993) "Cloning and characterization of a human protein phosphatase 1-encoding cDNA," Gene 129:291-295.
Stankovic et al. (2008) "Gene Expression Profiling of Nasal Polyps Associated With Chronic Sinusitis and Aspirin-Sensitive Asthma," The Laryngoscope 118:881-889.
Tai et al. (2005) "Periostin induction in tumor cell line explants and inhibition of in vitro cell growth by anti-periostin antibodies," Carcinogenesis 26(5):908-915.
Takayama et al. (2006) "Periostin: A novel component of subepithelial fibrosis of bronchial asthma downstream of IL-4 and IL-13 signals," J. Allergy Clin. Immunol. 118(1):98-104.
Takeshita et al. (1993) "Osteoblast-specific factor 2: cloning of a putative bone adhesion protein with homology with the insect protein fasciclin I," Biochem. J. 294:271-278.

(56) References Cited

OTHER PUBLICATIONS

Wang et al. (2004) "SU5416 is a potent inhibitor of hepatocyte growth factor receptor (c-Met) and blocks HGF-induced invasiveness of human HepG2 hepatoma cells," Journal of Hepatology 41:267-273.

Wang et al. (2006) "Expression Profile of Immune-Associated Genes in Nasal Polyps," Annals of Otology, Rhinology & Laryngology 115(6):450-456.

Wang, et al. (2003) "Potent and Selective Inhibitors of the Met [hepatocyte growth factor/scatter factor (HGF/SF) receptor] Tyrosine Kinase Block HGF/SF-Induced Tumor Cell Growth and Invasion" *Molecular Cancer Therapeutics*, 2:1085-1092.

Yuyama et al. (2002) "Analysis of novel disease-related genes in bronchial asthma," Cytokine 19(6):287-296.

Zarnegar and Michalopoulos (1995) "The Many Faces of Hepatocyte Growth Factor: from Hepatopoiesis to Hematopoiesis," The Journal of Cell Biology 129(5):1177-1180.

Figure 5

| Assay | N | Males (%) | Mean age (yrs±sd), range | Computed tomography stage (mean±sd) | History of asthma (%) | Prior sinus surgeries (mean±sd) |
|---|---|---|---|---|---|---|
| Microarray | | | | | | |
| CRS | 10 | 3 (30%) | 50.1±13 (28-73) | 3.4±0.5 | 1 (10%) | 1.7±2.4 |
| ASA | 10 | 3 (30%) | 45.5±10 (33-64) | 3.9±0.3 | 10 (100%) | 3.1±2.1 |
| Control | 10 | 5 (50%) | 40.7±19 (19-68) | 0 | 0 (0%) | 0 |
| Total | 30 | | | | | |
| PCR | | | | | | |
| CRS | 5 | 2 (40%) | 55.8±12 (36-66) | 3.8±0.5 | 4 (80%) | 0.6±0.84 |
| ASA | 7 | 1 (14%) | 51.7±13 (40-80) | 3.6±0.5 | 7 (100%) | 5.4±2.8 |
| Control | 5 | 1 (20%) | 47.2±7.7 (38-58) | 0 | 0 (0%) | 0 |
| Total | 17 | | | | | |
| IHS | | | | | | |
| CRS | 4 | 2 (50%) | 48±17 (34-73) | 4±0 | 2 (50%) | 2.25±2.1 |
| ASA | 4 | 0 (0%) | 52±20 (27-75) | 3.8±0.5 | 4 (100%) | 3.3±2.6 |
| Control | 2 | 0 (0%) | 45±2.8 (43-47) | 0 | 0 (0%) | 0 |
| Total | 10 | | | | | |

CRS=chronic rhinosinusitis
ASA=aspirin-sensitive asthma
IHS=immunohistochemistry

Figure 6

| GENE | CRS vs. CONTROLS (fold increase) | | ASA vs. CONTROLS (fold increase) | |
|---|---|---|---|---|
| | Microarray | qPCR | Microarray | qPCR |
| PIP | 0.05 (FDR <6%) | 0.003±0.003 (p=0.006) | 0.05 (FDR =9%) | 0.002±0.001 (p=0.001) |
| MET | 3.5 (FDR <6%) | 5.4±2.7 (p=0.01) | 3.4 (FDR =9%) | 1.0±0.4 (p=0.9) |
| AZGP1 | 0.04 (FDR <6%) | 0.05±0.04 (p=0.02) | 0.07 (FDR =9%) | 0.01±0.01 (p=0.002) |
| PPP1R9B | 31.5* (FDR <6%) | 2.9±1.3 (p=0.02) | 31.7* (FDR =9%) | 1.2±0.2 (p=0.5) |
| PERIOSTIN | 3.6 (FDR <6%) | 22.6±20.0 (p=0.01) | 3.6 (FDR =9%) | 4.5±2.8 (p=0.02) |

SEQUENCE LISTING

<160> NUMBER OF SEQ ID NOS: 2

<210> SEQ ID NO 1
<211> LENGTH: 171
<212> TYPE: PRT
<213> ORGANISM: Artificial sequence
<220> FEATURE:
<223> OTHER INFORMATION: Description of Artifical Sequence:
      Recombinant/Synthetic Peptide

<400> SEQUENCE: 1

Met Glu Pro Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
                20                  25                  30

Arg Pro Thr Pro Ala Thr Leu Val Leu Thr Ser Asp Gln Ser Ser Pro
            35                  40                  45

Glu Ile Asp Glu Asp Arg Ile Pro Asn Ser Leu Leu Lys Ser Thr Leu
    50                  55                  60

Ser Met Ser Pro Arg Gln Arg Lys Lys Met Thr Arg Thr Thr Pro Thr
65                  70                  75                  80

Met Lys Glu Leu Gln Thr Met Val Glu His His Leu Gly Gln Gln Lys
                85                  90                  95

Gln Gly Glu Glu Pro Glu Gly Ala Thr Glu Ser Thr Gly Asn Gln Glu
            100                 105                 110

Ser Cys Pro Pro Gly Ile Pro Asp Thr Gly Ser Ala Ser Arg Pro Asp
        115                 120                 125

Thr Pro Gly Thr Ala Gln Lys Ser Ala Glu Ser Asn Pro Lys Thr Gln
    130                 135                 140

Glu Gln Cys Gly Val Glu Pro Arg Thr Glu Asp Ser Ser Ala His Met
145                 150                 155                 160

Leu Pro Leu Asp Ser Gln Gly Ala Ser Leu Val
                165                 170

<210> SEQ ID NO 2
<211> LENGTH: 205
<212> TYPE: PRT
<213> ORGANISM: Artificial sequence
<220> FEATURE:
<223> OTHER INFORMATION: Description of Artifical Sequence:
      Recombinant/Synthetic Peptide

<400> SEQUENCE: 2

Met Ala Ala Ser Thr Ala Ser His Arg Pro Ile Lys Gly Ile Leu Lys
1               5                   10                  15

Asn Lys Thr Ser Ser Thr Ser Ser Arg Val Ala Ser Ala Glu Gln Pro
                20                  25                  30

Arg Gly Ser Val Asp Glu Glu Leu Ser Lys Lys Ser Gln Lys Trp Asp
            35                  40                  45

Glu Met Asn Ile Leu Ala Thr Tyr His Pro Ala Asp Lys Asp Tyr Gly
    50                  55                  60

Leu Met Lys Ile Asp Glu Pro Ser Thr Pro Tyr His Ser Met Ile Gly
65                  70                  75                  80

Asp Asp Asp Asp Ala Tyr Ser Asp Thr Glu Thr Thr Glu Ala Met Thr
                85                  90                  95

Pro Asp Thr Leu Ala Lys Lys Leu Ala Ala Ala Glu Gly Ser Glu Pro
            100                 105                 110

Lys Tyr Arg Ile Arg Glu Gln Glu Ser Ser Gly Glu Glu Asp Ser Asp

-continued

```
            115                 120                 125
Leu Ser Pro Glu Glu Arg Glu Lys Lys Arg Gln Phe Glu Met Lys Arg
        130                 135                 140

Lys Leu His Tyr Asn Glu Gly Leu Asn Ile Lys Leu Ala Arg Gln Leu
145                 150                 155                 160

Ile Ser Lys Asp Leu His Asp Asp Glu Glu Asp Glu Glu Met Ser Glu
                165                 170                 175

Thr Ala Asp Gly Glu Ser Met Asn Thr Glu Glu Ser Asn Gln Gly Ser
            180                 185                 190

Thr Pro Ser Asp Gln Arg Gln Asn Lys Ser Gln Ser Ser
        195                 200                 205
```

METHODS FOR TREATING POLYPS

CROSS-REFERENCE TO RELATED APPLICATIONS

This application is a continuation of U.S. patent application Ser. No. 12/863,415, filed Jan. 18, 2011, which is the U.S. national stage of International Patent Application PCT/US2009/031349, filed Jan. 16, 2009, which claims priority to and the benefit of U.S. Provisional Patent Application No. 61/011,568, filed Jan. 18, 2008, the disclosures of each of which are incorporated herein by reference in their entirety.

FIELD OF THE INVENTION

The invention relates generally to methods and compositions for treating sinusitis, asthma, or polyps, and, more specifically, the invention relates to methods and compositions for treating nasal polyps.

BACKGROUND

Sinusitis is one of the most commonly diagnosed diseases in the United States, affecting an estimated 37 million people each year. Studies have demonstrated the major economic impact of this disorder, which can dramatically reduce workplace productivity and quality of life in affected individuals. Patients with chronic sinusitis whose symptoms are most refractory to treatment regimens often develop nasal polyps. Growth of these polyps leads to obstruction of the sinonasal passages, requiring repeated courses of antibiotics to treat underlying infections and steroid therapy to reduce polyp load. In advanced cases, surgery may be necessary to remove the polyps and restore sinus ventilation. Histologically, sinonasal polyps are characterized by proliferation and thickening of mucosal epithelium with focal squamous metaplasia, glandular hyperplasia, subepithelial fibrosis, and stromal edema with numerous blood vessels (Bateman et al. (2003), *J. Laryngol. Otol.*, 117(1):1-9).

Most patients who develop nasal polyps have chronic rhinosinusitis. Nasal airway obstruction and drainage are common presenting symptoms. Anosmia and episodic facial pressure may also be present. A subset of these patients are diagnosed with aspirin-sensitive asthma, also known as Triad asthma and Samter's triad, characterized by the presence of nasal polyps, asthma, and aspirin allergy. When individuals with this disorder take aspirin (or non-steroidal anti-inflammatory drugs in many cases) immediate and severe bronchospasm results, often necessitating treatment in the emergency room. It has been hypothesized that a common stimulus is causing inflammation of both the sinonasal and bronchopulmonary mucosa (Krouse et al. (2007), *Otolaryngol. Head Neck Surg.*, 136(5):699-706).

Currently, treatment of nasal polyps with antibiotics, steroids, allergy shots and even surgery is typically unsatisfactory. Antibiotics require repeated courses and systemic administration, which increases the risk of developing antibiotic resistance and secondary yeast infections. Antibiotics also do not eliminate polyps once they are formed. Steroids reduce but do not eliminate polyps. When given systemically for a long period of time, steroids have many severe side effects including elevation of blood pressure, insomnia, agitation, psychosis, increased susceptibility to infection, easy bruising, weight gain, osteoporosis and joint damage, hyperglycemia and worsening diabetes, cataracts, and muscular weakness. When given intranasally, steroids can cause thinning of the nasal mucosa with subsequent bleeding. In addition, intranasal steroids are not as effective as systemic steroids. Immunotherapy (e.g., allergy shots) is helpful in reducing but not eliminating polyp load in a subset of patients with nasal polyps and evidence of significant allergic triggers. Immunotherapy involves a series of injections (shots) given regularly for several years. Side effects can be severe and include difficulty in breathing, arrhythmia and death. Surgery is used when other medical therapies fail. The risk of surgery includes injury to the eye or brain, spinal fluid leak, loss of sense of smell and nosebleeds in addition to the risks associated with general anesthesia. Furthermore, nasal polyps tend to regrow in at least one-third of patients, often necessitating repeat surgeries.

Thus, sinonasal disease is a problem of major clinical and societal impact for which curative therapeutic modalities are lacking. Microarray technology has revolutionized the field of genetic analysis, making it possible to quantify the simultaneous expression of thousands of genes and is a powerful tool for disease studies. However, prior studies of sinonasal tissue that used this technology focused on subsets of the genome and limited patient populations with upper airway disease (Fritz et al. (2003), *J. Allergy Clin. Immunol.*, 112(6): 1057-63; Liu et al. (2004), *J. Allergy Clin. Immunol.*, 114(4): 783-90; Benson et al. (2004), *J. Allergy Clin. Immunol.*, 113 (6):1137-43; Wang et al. (2006), *Ann. Otol. Rhinol. Laryngol.*, 115(6):450-6; Anand et al. (2006), *Am. J. Rhinol.*, 20(4):471-6; Figueiredo et al. (2007), *Am. J. Phinol.*, 21(2): 231-5; Orlandi et al. (2007), *Otolaryngol. Head Neck Surg.*, 136(5):707-13; Bolger et al. (2007), *Otolaryngol. Head Neck Surg.*, 137(1):27-33).

SUMMARY OF THE INVENTION

In the context of present invention, high throughput microarray technology validated by real-time quantitative PCR (RT-qPCR) and immunostaining was used to identify five genes, periostin, met-proto-oncogene (MET), zinc alpha2-glycoprotein (AZGP1), prolactin-induced protein (PIP) and protein phosphatase 1 regulatory subunit 9B (PPP1R9B), as well as the proteins encoded by these genes, that play roles in the pathogenesis of polyps, such as nasal polyps, such as those associated with chronic rhinosinusitis (CRS) and those additionally associated with aspirin-sensitive asthma (ASA). These genes and/or their products are targets for therapies to treat polyps. Insofar as the MET, periostin and protein phosphatase 1 regulatory 9B (PPP1R9B) genes are upregulated in those with polyps, therapies which inhibit the transcription of these genes, the expression of the proteins encoded by these genes, or the activity of the proteins encoded by these genes or the biological regulatory systems (upstream and downstream) to which they belong (i.e., downregulate the transcription, expression, or activity of the targets) are useful. Similarly, as the AZGP1 and PIP genes are downregulated in those with polyps, therapies which add exogenous proteins encoded by these genes, or increase the transcription of these genes, the expression of the proteins encoded by these genes, or the activity of the proteins encoded by these genes or the biological regulatory systems (upstream and downstream) to which they belong (i.e., upregulate the amount, transcription, expression, or activity of the targets), are useful. It should be understood that initial empirical data indicated upregulation of the protein phosphatase 1 regulatory subunit 6 (PPP1R6) gene in addition to the PPP1R9B gene. Thus, in addition to PPP1R9B as a target, protein phosphatase 1 (PP1) generally, PPP1R6, and protein phosphatase 1 catalytic subunit (PP1c) are also targets. The therapies described above and below for PPP1R9B therefore are equally applicable to these three targets.

In one aspect, the invention provides a method for treating a polyp. The method includes administering to a subject who has or is suspected of developing a polyp an agent in an amount sufficient to attenuate growth of the polyp or to regress the polyp. The polyp may be, for example, a nasal polyp. In certain embodiments, the subject may have sinusitis, such as chronic rhinosinusitis or chronic rhinosinusitis with aspirin-sensitive asthma. In some embodiments, the subject may have asthma, such as a history of aspirin-sensitive asthma Another aspect the invention provides a method for treating sinusitis. The method includes administering to a subject having or suspected of developing sinusitis at least one agent selected from an antagonist of periostin, an antagonist of protein phosphatase 1, an antagonist of MET, an agonist of prolactin-induced protein, and an agonist of zinc alpha2-glycoprotein in an amount sufficient to alleviate a symptom of the sinusitis. The symptom can be a nasal polyp. In certain embodiments, the subject may have chronic rhinosinusitis or chronic rhinosinusitis with aspirin-sensitive asthma.

Another aspect of the invention provides a method for treating asthma. The method includes administering to a subject having or suspected of developing asthma at least one agent selected from an antagonist of periostin, an antagonist of protein phosphatase 1, an antagonist of MET, an agonist of prolactin-induced protein, and an agonist of zinc alpha2-glycoprotein in an amount sufficient to alleviate a symptom of the asthma. The symptom can be a nasal polyp, and the subject can have aspirin-sensitive asthma.

Another aspect of the invention provides a method for downregulating periostin, downregulating protein phosphatase 1, downregulating MET, upregulating prolactin-induced protein, or upregulating zinc alpha2-glycoprotein in polyp tissue. The method includes delivering at least one agent selected from an antagonist of periostin, an antagonist of protein phosphatase 1, an antagonist of MET, an agonist of prolactin-induced protein, and an agonist of zinc alpha2-glycoprotein to the polyp tissue in an amount sufficient to downregulate periostin, downregulate protein phosphatase 1, downregulate MET, upregulate prolactin-induced protein, upregulate zinc alpha2-glycoprotein, or a combination thereof in the polyp tissue. In certain embodiments, downregulating includes inhibiting gene transcription, protein expression, and/or protein activity of a target, and upregulating includes increasing gene transcription of a target, protein expression of a target, protein activity of a target, and/or adding exogenous proteins.

The aspects of the invention described above can have any of the following features. The subject may be a mammal, and more particularly, a human being. The agent can be administered locally or systemically. In certain embodiments, the agent may be an antagonist of periostin. For example, an antagonist of periostin can be an anti-periostin antibody, valsartan, or a small interfering RNA. The agent may also be an antagonist of PP1 (such as antagonists of PP1c, PPP1R9B, or PPP1R6). For example, antagonists of PP1 can be an anti-PP1 antibody, such as an anti-PP1c antibody, anti-PPP1R9B antibody or anti-PPP1R6 antibody; a protein phosphatase inhibitor, such as okadaic acid or calyculin A; dopamine-and cyclic AMP-regulated phosphoprotein (DARPP-32); a small interfering RNA, such as an anti-PP1c small interfering RNA, an anti-PPP1R9B small interfering RNA, or an anti-PPP1R6 small interfering RNA; or an inhibitory peptide such as a peptide comprising the amino acid sequence of MEP-DNSPRKIQFTVPLLEPHLDPEAAEQIR-RRRPTPATLVLTSDQSSPEIDEDRIP-NSLLKSTLSMSPRQRKKMTRTTPTMKELQTMVEHH-LGQQKQGEEPEGATESTGNQESCPPGIP-DTGSASRPDTPGTAQKSAESNPK-TQEQCGVEPRTEDSSAHMLPLDSQGASLV (SEQ ID NO:1) or a peptide comprising the amino acid sequence of MAASTASHRPIKGILKNKTSSTSSRVA-SAEQPRGSVDEELSKKSQKWDEMNI-LATYHPADKDYGLMKIDEPSTPYH-SMIGDDDDAYSDTETTEAMTPDTLAKKLAAAEGSEP-KYRIREQESSGEEDSDL-SPEEREKKRQFEMKRKLHYNEGLNI-KLARQLISKDLHDDEEDEEMSETADG-ESMNTEESNQGSTPSDQRQNKSQSS (SEQ ID NO:2). The agent also may be an antagonist of MET. For example, the MET antagonist can be an antisense nucleic acid; a small interfering RNA; an anti-MET antibody; or a tyrosine kinase inhibitor, such as (3Z)-N-(3-Chlorophenyl)-3-((3,5-dimethyl-4-((4-methylpiperazin-1-yl)carbonyl)-1H-pyrrol-2-yl) methylene)-N-methyl-2-oxo-2,3-dihydro-1H-indole-5-sulfonamide (SU11274) or 1,3-Dihydro-3-((3,5-dimethyl-1H-pyrrol-2-yl)methylene)-2H-indol-2-one (SU5416). In certain embodiments, the agent may also be an agonist of PIP. For example, the PIP agonist can be exogenous PIP protein or a stimulator of PIP protein production, such as interleukin-4, interleukin-13, or tamoxifen. The agent also may be an agonist of AZGP1. For example, the AZGP1 agonist can be exogenous AZGP1 protein or a stimulator of AZGP1 protein production, such as dexamethasone, rosiglitazone, or (RR+SS)-(±)-4-(2-((2-(3-chlorophenyl)-2-hydroxyethyl)amino) propyl)phenoxyacetate (BRL-37344). The class of agonists of zinc alpha2-glycoproteins, such as a stimulator of AZGP1 protein production, can exclude a steroid.

Figure 1:
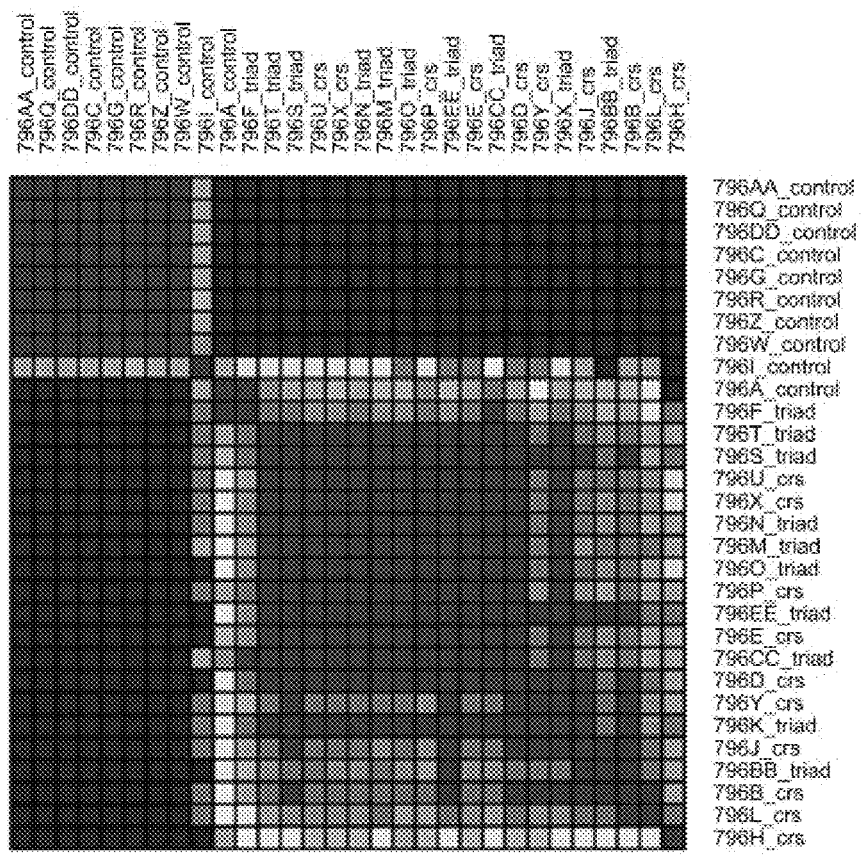
FIG. 1 is a heat map of samples that share similar patterns of gene expression. The bright red color (generally in the small upper left quadrant and in the large lower right quadrant) indicates samples that always clustered together, whereas the dark blue color (generally in the rectangular upper right quadrant and the rectangular lower left quadrant) indicates samples that never clustered together. Consensus hierarchical clustering was performed assuming three clusters. Control samples formed a distinct cluster (upper red block) whereas the chronic rhinosinusitis (CRS) and aspirin-sensitive asthma (ASA; Triad in the figures) samples intermingled (lower red block).

met-proto-oncogene (MET): protein phosphatase 1 regulatory subunit 9B (PPP1R9B)=97:46:37:1.3:1.

FIGS. 4A-O are representative photographs showing sinonasal polyps and control sinonasal mucosa immunostained with antibodies against periostin (OSF, A-C), MET (Met, D-F), prolactin-induced protein (PIP, G-I), zinc alpha2-glycoprotein (ZAG, J-L), and neurabin 2 (PPP, M-O; also known as PPP1R9B). Scale bar=100 µm.

FIG. 5 is a table showing patient demographics for the microarray (n=30), RT-qPCR (n=17), and immunohistochemistry (n=10) analyses.

FIG. 6 is a table showing fold increase in expression of genes most characteristic of the CRS and ASA groups as compared with the control group and determined from microarray and RT-qPCR analysis. The asterisk indicates microarray results for the sequence from clone RP4-551D2 on chromosome 20q13.2-13.33 that contains a gene for PPP1R6. "FDR" means false detection rate. For RT-qPCR, the data are expressed as mean+/−standard error of the mean.

DETAILED DESCRIPTION OF THE INVENTION

Using genome-wide expression profiling of nasal polyps, five genes that play roles in the pathogenesis of polyps were identified. These genes and their protein products are targets for therapies for polyps, such as nasal polyps, such as those associated with chronic sinusitis and aspirin-sensitive asthma. The therapies also can be used for treatment of inflammatory polyps in the middle ear. More generally, the therapies can be used to treat (locally or systemically) polyps and tumors throughout the body. It should be understood that although much of the specification discusses nasal polyps, it is contemplated that the methods and compositions described herein are broadly applicable to polyps and tumors throughout the body.

The five genes that have been identified are: MET, periostin, PIP, AZGP1 and PP1. In particular, compared with expression level in normal sinonasal mucosa, three genes in nasal polyps, MET, periostin and PP1, are upregulated, whereas the other two genes in nasal polyps, AZGP1 and PIP, are downregulated. It should be understood that while the PPP1R9B and PPP1R6 genes were found empirically to be upregulated, the PPP1R9B gene, the PPP1R6 gene, as well as any other genes for regulatory and catalytic subunits or subunit subtypes of PP1, such as PP1c, and the proteins which they encode, are targets according to the invention. Accordingly, the text refers to PP1 as the target for convenience but should be understood to relate to PP1 generally, PPP1R9B, PPP1R6, PP1c, or any other PP1 subunits or subunit subtypes.

Therapies targeting these genes and their protein products can treat and/or prevent polyps, including nasal polyps. In the case of the upregulated genes, therapies include those that decrease the transcription of the gene, decrease the translation of the gene into a protein, or inhibit the activity of the protein or the biological regulatory system (upstream and downstream) in which it resides. More generally, antagonists are used against the upregulated genes or the proteins that they encode. In the case of the downregulated genes, therapies include those that increase the transcription of the gene, increase the translation of the gene into a protein, or stimulate the activity of the protein or the biological regulatory system (upstream and downstream) in which it resides as well as include provision of an exogenous form of the protein, including the protein itself, those proteins or peptides that are at least 85%, 90%, or 95% identical to the full length, wild type sequence of the protein, and those proteins or peptides that have at least 25%, more preferably at least 50%, more preferably at least 75%, and more preferably at least 90% activity of the full length, wild type protein. More generally, agonists are used to target the downregulated genes or the proteins that they encode. In the case of nasal polyps, these therapies may be delivered topically into the nose to prevent systemic side effects, or systemically if the side-effect profile is safe and tolerable. Various agonists and antagonists useful as treatment agents according to methods of the invention are described in more detail, below.

Methods for treating a polyp include administering to a subject having, or suspected of developing, a polyp a treatment agent in an amount sufficient to attenuate growth of the polyp or to regress the polyp. Regression of the polyp can be either partial or complete regression. Partial regression can be, for example, reduction in the volume of the polyp, whereas complete regression can be elimination of the polyp or returning the tissue to its pre-polyp state. Treatment agents include periostin antagonists, PP1 antagonists (such as PP1c antagonists, PPP1R9B antagonists or PPP1R6 antagonists), and MET antagonists as well as PIP agonists and AZGP1 agonists. Treatments according to the invention are useful in treating mammals, including humans.

Given that the five genes were identified in disease-state tissue from those having sinusitis (i.e., chronic rhinosinusitis) and from those having asthma (i.e., chronic rhinosinusitis with aspirin-sensitive asthma), the treatments discussed herein with regard to polyps, such as nasal polyps, such as those associated with chronic sinusitis and aspirin-sensitive asthma, are equally applicable for treating sinusitis or asthma generally, for example by alleviating a symptom of sinusitis or asthma, such as a nasal polyp. Thus, a method for treating sinusitis includes administering to a subject having or suspected of developing sinusitis at least one agent selected from an antagonist of periostin, an antagonist of protein phosphatase 1, an antagonist of MET, an agonist of prolactin-induced protein, and an agonist of zinc alpha2-glycoprotein in an amount sufficient to alleviate a symptom of the sinusitis. The subject may have any type of sinusitis, such as maxillary sinusitis, frontal sinusitis, ethmoid sinusitis, or sphenoid sinusitis. Sinusitis also may be acute, for example as caused by upper respiratory tract infection, dental problems that affect the maxillary sinus, or fungal invasion, or may be chronic, for example as caused by allergy, environmental factors such as dust or pollution, bacterial infection, or fungus (either allergic, infective, or reactive). In certain embodiments, the subject may have chronic rhinosinusitis or chronic rhinosinusitis with aspirin-sensitive asthma. Symptoms of sinusitis can include a nasal polyp; facial pain or pressure (for example, in the forehead, temples, cheeks, nose or behind the eyes); headache; fever; pain, tenderness or swelling around the eyes, cheeks, nose or forehead; ear pain; erythema (or redness of the skin over the sinus caused by increased blood flow to the capillaries); nasal congestion or obstruction; difficulty breathing through the nose; reduced sense of smell or taste; dental pain (for example, aching in the upper jaw and teeth); cough; bad breath (halitosis); fatigue; nausea; sore throat; and/or drainage of a thick, yellow or greenish discharge from the nose or down the back of the throat.

Additionally, a method for treating asthma includes administering to a subject having or suspected of developing asthma at least one agent selected from an antagonist of periostin, an antagonist of protein phosphatase 1, an antagonist of MET, an agonist of prolactin-induced protein, and an agonist of zinc alpha2-glycoprotein in an amount sufficient to alleviate a symptom of the asthma. The subject may have any kind of asthma, such as allergic asthma; intrinsic asthma (Where allergies do not play a part. Possible causes of intrinsic asthma include respiratory irritants such as perfumes, cleaning agents, fumes, smoke and cold air, upper respiratory infections, and gastroesophageal reflux (GERD)); exercise-induced asthma; nocturnal asthma (for example, during sleep); occupational asthma (breathing chemical fumes, wood dust, or other irritants over long periods of time); or steroid-resistant asthma (overuse of asthma medications leading to status asthmaticus). In certain embodiments, the subject may have aspirin-sensitive asthma. Symptoms of asthma can include a nasal polyp; fatigue; itchy throat; runny nose; headache; chest tightness; change in the color, amount, or thickness of mucus; wheezing; coughing; shortness of breath; tightness in the chest; lack of oxygen; chest pain; and/or loss of consciousness.

The nucleic acid encoding MET is understood to be approximately 125 kb in length and includes 21 exons and 20 introns (as reported in the NCBI gene database for gene ID: 4233, which is incorporated herein by reference). MET has two alternatively spliced transcript variants. The protein encoded by transcript variant 1 is 1390 amino acids in length (as reported in the NCBI protein database for NP_000236, which is incorporated herein by reference); and the protein encoded by transcript variant 2 is 1408 amino acids in length (as reported in the NCBI protein database for NP_001120972, which is incorporated herein by reference). Thus, the sequence of the nucleic acid encoding MET and the sequences of the MET proteins are known in the art (see also Bottaro et al. (1991), *Science*, 251(4995):802-4, which is incorporated herein by reference).

The nucleic acid encoding periostin is understood to be approximately 36 kb in length and includes 23 exons and 22 introns (as reported in the NCBI gene database for gene ID: 10631, which is incorporated herein by reference). Periostin has four alternatively spliced transcript variants. The protein encoded by variant 1 is 836 amino acids in length (as reported in the NCBI protein database for NP_006466, which is incorporated herein by reference); the protein encoded by transcript variant 2 is 779 amino acids in length (as reported in the NCBI protein database for NP_001129406, which is incorporated herein by reference); the protein encoded by variant 3 is 781 amino acids in length (as reported in the NCBI protein database for NP_001129407, which is incorporated herein by reference); and the protein encoded by variant 4 is 751 amino acid in length (as reported in the NCBI protein database for NP_001129408, which is incorporated herein by reference). Thus, the sequence of the nucleic acid encoding periostin and the sequences of the periostin proteins are known in the art (see also Takeshita et al. (1993), *Biochem. J.*, 294:271-8, which is incorporated herein by reference).

The nucleic acid encoding PIP is understood to be 7661 base pairs in length and includes 4 exons and 3 introns (as reported in the NCBI gene database for gene ID: 5304, which is incorporated herein by reference). PIP itself is 146 amino acids in length (as reported in the NCBI protein database for NP_002643, which is incorporated herein by reference). Thus, the sequence of the nucleic acid encoding PIP and the sequence of PIP are known in the art (see also Murphy et al. (1987), *J. Biol. Chem.*, 262(31):15236-41, which is incorporated herein by reference).

The nucleic acid encoding AZGP1 is understood to be 9338 base pairs in length and includes 4 exons and 3 introns (as reported in the NCBI gene database for gene ID: 563, which is incorporated herein by reference). The AZGP1 protein itself is 298 amino acids in length (as reported in the NCBI protein database for NP_001176, which is incorporated herein by reference). Thus, the sequence of the nucleic acid encoding AZGP1 and the sequence of the AZGP1 are known in the art (see also Araki et al. (1988), *PNAS* (USA), 85:679-83, which is incorporated herein by reference).

The nucleic acid encoding PPP1R9B is understood to be approximately 17 kb in length and includes 10 exons and 9 introns (as reported in the NCBI gene database for gene ID: 84687, which is incorporated herein by reference). The PPP1R9B protein itself is 817 amino acids in length (as reported in the NCBI protein database for NP_115984, which is incorporated herein by reference). Thus, the sequence of the nucleic acid encoding PPP1R9B and the sequence of the PPP1R9B protein are known in the art (see also Allen et al. (1997), *PNAS* (USA), 94:9956-61, which is incorporated herein by reference).

The nucleic acid encoding PPP1R6 is understood to be 3466 base pairs in length and includes 1 exon (as reported in the NCBI gene database for gene ID: 5509, which is incorporated herein by reference). The PPP1R6 protein itself is 299 amino acids in length (as reported in the NCBI protein database for NP_006233, which is incorporated herein by reference). Thus, the sequence of the nucleic acid encoding PPP1R6 and the sequence of the PPP1R6 protein are known in the art (see also Armstrong et al. (1997), *FEBS Lett.*, 418:210-4, which is incorporated herein by reference).

PP1c has alpha, beta and gamma isoforms, which are encoded by different genes. The nucleic acid encoding PP1c alpha isoform (PPP1CA) is understood to be 3752 base pairs in length and includes 7 exons and 6 introns (as reported in the NCBI gene database for gene ID: 5499, which is incorporated herein by reference). PPP1CA has three alternatively spliced transcript variants. The protein encoded by transcript variant 1 is 330 amino acids in length (as reported in the NCBI protein database for NP_002699, which is incorporated herein by reference); the protein encoded by transcript variant 2 is 286 amino acids in length (as reported in the NCBI protein database for NP_996756, which is incorporated herein by reference); and the protein encoded by transcript variant 3 is 341 amino acid in length (as reported in the NCBI protein database for NP_001008709, which is incorporated herein by reference). Thus, the sequence of the nucleic acid encoding PPP1CA and the sequences of the PPP1CA proteins are known in the art (see also Song et al. (1993), *Gene*, 129(2):291-5, which is incorporated herein by reference).

The nucleic acid encoding PP1c beta isoform (PPP1CB) is understood to be approximately 50 kb in length and includes 8 exons and 7 introns (as reported in the NCBI gene database for gene ID: 5500, which is incorporated herein by reference). PPP1CB has two alternatively spliced transcript variants. Transcript variants 1 and 2 encode the same protein, which is 327 amino acid in length (as reported in the NCBI protein database for NP_002700 and NP_996759, respectively, which are incorporated herein by reference). Thus, the sequence of the nucleic acid encoding PPP1CB and the sequence of the PPP1CB protein are known in the art (see also Barker et al. (1994), *Biochem. Biophys. Acta.*, 1220(2):212-8, which is incorporated herein by reference).

The nucleic acid encoding PP1c gamma isoform (PPP1CC) is understood to be approximately 23 kb in length and includes 7 exons and 6 introns (as reported in the NCBI gene database for gene ID: 5501, which is incorporated herein by reference). The PPP1CC protein itself is 323 amino acids in length (as reported in the NCBI protein database for NP_002701, which is incorporated herein by reference). Thus, the sequence of the nucleic acid encoding PPP1CC and the sequence of the PPP1CC protein are known in the art (see also Barker et al. (1993), *Biochem. Biophys. Acta.*, 1178(2):228-33, which is incorporated herein by reference).

Herein, to determine whether a candidate protein or peptide has the requisite percentage similarity or identity to a reference polypeptide or peptide oligomer, the candidate amino acid sequence and the reference amino acid sequence are first aligned using the dynamic programming algorithm described in Smith et al. (1981), *J. Mol. Biol.*, 147:195-7, in combination with the BLOSUM62 substitution matrix described in FIG. 2 of Henikoff et al. (1992), *PNAS* (USA), 89:10915-9. An appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

I. Treatment Agents

The term "treatment agent" is understood to mean any molecule, for example, a protein, peptide, nucleic acid (ribonucleic acid (RNA) or deoxyribonucleic acid (DNA)), peptidyl nucleic acid, or small molecule (organic compound or inorganic compound). Treatment agents can be antagonists that, either directly or indirectly, decrease the transcription of a gene, the translation of the gene into a protein, or the activity of the protein or the biological regulatory system (upstream and downstream) in which it resides (i.e., downregulate the transcription, translation, or activity of the target of interest). Antagonists can be used against the three upregulated genes or their expression products, namely against the MET, periostin, and PP1 (such as PP1c, PPP1R9B or PPP1R6) genes or the MET, periostin, and PP1 (such as PP1c, PPP1R9B or PPP1R6) proteins. Alternatively, treatment agents can be agonists that, either directly or indirectly, increase the transcription of the gene, the translation of the gene into a protein, or the activity of the protein or the biological regulatory system (upstream and downstream) in which it resides as well as can include provision of an exogenous form of the protein, including the protein itself, those proteins or peptides that are at least 85%, 90%, or 95% identical to the full length, wild type sequence of the protein, and those proteins and peptides that have at least 25%, more preferably at least 50%, more preferably at least 75%, and more preferably at least 90% activity of the full length, wild type protein (i.e., upregulate the transcription, translation, activity, or amount of the target of interest). Agonists can be used to target the two downregulated genes or their gene expression products, namely the PIP and AZGP1 genes or the PIP and AZGP1 proteins. In the invention, an effective amount of treatment agent is used in a subject for a therapeutic purpose. Accordingly, an "effective amount" of an treatment agent is an amount of an agent sufficient to attenuate growth of a polyp or to regress a polyp. Alternatively, an "effective amount" of a treatment agent is an amount of an agent sufficient to alleviate a symptom of sinusitis or of asthma.

1) Exemplary Treatment Agents—proteins

Antibodies (e.g., monoclonal or polyclonal antibodies) having sufficiently high binding specificity for a target protein, can be used as a treatment agent. For example, anti-MET, anti-periostin or anti-PP1 (such as anti-PP1c, anti-PPP1R9B or anti-PPP1R6) antibodies, can be used as antagonists. As noted above, the term "antibody" is understood to mean an intact antibody (for example, a monoclonal or polyclonal antibody); an antigen binding fragment thereof, for example, an Fv, Fab, Fab' or (Fab')$_2$ fragment; or a biosynthetic antibody binding site, for example, an sFv, as described in U.S. Pat. Nos. 4,704,692; 5,091,513; 5,132,405; 5,258,498; and 5,482,858. A binding moiety, for example, an antibody, is understood to bind specifically to the target, for example, MET, periostin or PP1 (such as PP1c, PPP1R9B or PPP1R6), when the binding moiety has a binding affinity for the target greater than about $10^5$ $M^{-1}$, more preferably greater than about $10^7$ $M^{-1}$. Those antibodies that act with agonistic activity also can be used, for example, when PIP or AZGP1 are targets.

The aforementioned antibodies may be generated using standard immunological procedures well known and described in the art See, for example, *Practical Immunology*, Butt, N. R., ed., Marcel Dekker, NY, 1984. Briefly, isolated MET, periostin, PP1 (such as PP1c, PPP1R9B or PPP1R6), PIP, or AZGP1 is used to raise antibodies in a xenogeneic host, such as a mouse, goat or other suitable mammal. The target protein (e.g., MET, periostin, PP1 (such as PP1c, PPP1R9B or PPP1R6), PIP, or AZGP1) is combined with a suitable adjuvant capable of enhancing antibody production in the host, and injected into the host, for example, by intraperitoneal administration. Any adjuvant suitable for stimulating the host's immune response may be used. A commonly used adjuvant is Freund's complete adjuvant (an emulsion comprising killed and dried microbial cells). Where multiple antigen injections are desired, the subsequent injections may comprise the antigen in combination with an incomplete adjuvant (for example, a cell-free emulsion).

Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target protein and have the desired binding affinity.

Antibody binding domains also may be produced biosynthetically and the amino acid sequence of the binding domain manipulated to enhance binding affinity with a preferred epitope on the target protein. Specific antibody methodologies are well understood and described in the literature. A more detailed description of their preparation can be found, for example, in *Practical Immunology*, Butt, W. R., ed., Marcel Dekker, New York, 1984.

Other proteins and peptides also can be used as treatment agents, such as agonists of PIP or AZGP1 or antagonists of MET, periostin, or PP1 (such as PP1c, PPP1R9B or PPP1R6).

In the case of agonists of PIP or AZGP1, the agonist can be the PIP or AZGP1 protein itself, can be a protein or peptide that is at least 85%, 90%, or 95% identical to the full length, wild type sequence of PIP or AZGP1 or can be a protein or peptide that has at least 25%, more preferably at least 50%, more preferably at least 75%, and more preferably at least 90% activity of full length, wild type PIP or AZGP1 protein. Proteins and peptides of the invention can be produced in various ways using approaches known in the art. For example, DNA molecules encoding the protein or peptide of interest are chemically synthesized, using a commercial synthesizer and known sequence information. Such synthetic DNA molecules can be ligated to other appropriate nucleotide sequences, including, e.g., expression control sequences, to produce conventional gene expression constructs encoding the desired proteins and peptides. Production of defined gene constructs is within routine skill in the art.

The nucleic acids encoding the desired proteins and peptides can be introduced (ligated) into expression vectors, which can be introduced into a host cell via standard transfection or transformation techniques known in the art. Exemplary host cells include, for example, *E. coli* cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce immunoglobulin protein. Transfected host cells can be grown under conditions that permit the host cells to express the genes of interest, for example, the genes that encode the proteins or peptides of interest. The resulting expression products can be harvested using techniques known in the art.

The particular expression and purification conditions will vary depending upon what expression system is employed. For example, if the gene is to be expressed in *E. coli*, it is first cloned into an expression vector. This is accomplished by positioning the engineered gene downstream from a suitable bacterial promoter, e.g., Trp or Tac, and a signal sequence, e.g., a sequence encoding fragment B of protein A (FB). The resulting expressed fusion protein typically accumulates in refractile or inclusion bodies in the cytoplasm of the cells, and may be harvested after disruption of the cells by French press or sonication. The refractile bodies then are solubilized, and the expressed proteins refolded and cleaved by the methods already established for many other recombinant proteins.

If the engineered gene is to be expressed in eukaryotic host cells, for example, myeloma cells or CHO cells, it is first inserted into an expression vector containing a suitable eukaryotic promoter, a secretion signal, and various introns. The gene construct can be transfected into myeloma cells or CHO cells using established transfection protocols. Such transfected cells can express the proteins or peptides of interest, which may be attached to a protein domain having another function.

A variety of the aforementioned protein treatment agents, including antibodies, inhibitory proteins/peptides and exogenous proteins, are described in the art. For example, MET antagonists include, but are not limited to, polyclonal antibodies against human MET (available from Santa Cruz Biotechnology, Inc, Santa Cruz, Calif., Cat. No.: SC-10) and anti-MET antibody (available from Sigma-Aldrich, St. Louis, Mo., Cat. No.: C7115) (see also Colombo et al. (2007), *Invest. Ophthalmol. Vis. Sci.,* 48:1793-1800). Periostin antagonists include, but are not limited to, polyclonal antibodies against human periostin (available from BioVendor Laboratory Medicine, Inc, Modrice, Czech Republic, Cat. No.: RD-181045050) and anti-periostin monoclonal antibody (see Tai et al. (2005), *Carcinogenesis*, 26(5):908-15). PP1 antagonists include, but are not limited to, polyclonal antibodies against human neurabin 2 (also known as PPP1R9B) (available from Abeam, Inc, Cambridge, Mass., Cat. No.: AB18561), anti-PPP1R9B antibody (available from Novus Biological, Inc., Littleton, Co; Cat. No. H00084687-A01), inhibitory peptides specific for PP1, such as a peptide including the amino acid sequence of MEPDNSPRKIQFTVPLLE-PHLDPEAAEQIRRRRPTPATLVLTS-DQSSPEIDEDRIPNSLLKSTLSMSPRQRKKMTRTTPT-MKELQTMVEHHLGQQKQGEEPEGATEST-GNQESCPPGIPDTGSASRPDTPGTAQK-SAESNPKTQEQCGVEPRTEDSSAHMLPLDSQGASLV) (SEQ ID NO:1) (Inhibitor-1) (see also Alberts et al.(1994), MCB, 14(7):4398-407) and a peptide including the amino acid sequence of MAASTASHRPIKGILKNKTSSTSSRVA-SAEQPRGSVDEELSKKSQKWDEMNI-LATYHPADKDYGLMKIDEPSTPYH-SMIGDDDDAYSDTETTEAMTPDTLAKKLAAAEGSEP-KYRIREQESSGEEDSDL-SPEEREKKRQFEMKRKLHYNEGLNI-KLARQLISKDLHDDEEDEEMSETADG-ESMNTEESNQGSTPSDQRQNKSQSS (SEQ ID NO:2) (Inhibitor-2); and dopamine-and cyclic AMP-regulated phosphoprotein (DARPP-32) (available from EMD Calbiochem, Inc., Gibbstown, N.J.; Cat. No. 251755). PIP agonists include, but are not limited to, the PIP protein, recombinant PIP protein (available from Abnova, Taipei City, Taiwan, Cat. No.: H00005304-P01), and stimulators of PIP expression such as interleukin-4 (available from Sigma-Aldrich, St. Louis, Mo., Cat. No. 14269) and interleukin-13 (available from Sigma-Aldrich, St. Louis, Mo., Cat. No. 11771) (see also Blais et al. (1996), *Mol. Cell. Endocrinol.,* 121(1):11-18). AZGP1 agonists include, but are not limited to, the AZGP1 protein, recombinant AZGP1 protein (available from Abnova, Taipei City, Taiwan, Cat. No.: H00000563-P01) (see also He et al. (2001), *J. Cell Biochem.,* 81:162-9).

2) Exemplary Treatment Agent—Nucleic Acids

To the extent that the treatment agent is a nucleic acid or peptidyl nucleic acid, such compounds may be synthesized by any of the known chemical oligonucleotide and peptidyl nucleic acid synthesis methodologies known in the art (see, for example, PCT/EP92/20702 and PCT/US94/013523) and used in antisense therapy. Anti-sense oligonucleotide and peptidyl nucleic acid sequences, usually 10 to 100 and more preferably 15 to 50 units in length, are capable of hybridizing to a gene and/or mRNA transcript and, therefore, may be used to inhibit transcription and/or translation of a target gene/protein. MET, periostin or PP1 (such as PP1c, PPP1R9B or PPP1R6) gene expression can therefore be inhibited by using nucleotide sequences complementary to a regulatory region of any of these genes (e.g., the promoter and/or a enhancer) to form triple helical structures that prevent transcription of any of these gene in target cells. See generally, Helene (1991), *Anticancer Drug Des.,* 6(6): 569-84, Helene et al. (1992), *Ann. N.Y. Acad. Sci.,* 660: 27-36; and Maher (1992), *Bioessays,* 14(12): 807-15. Anti-sense sequences that act with agonistic activity also may be used as a treatment agent, for example, as agonists for PIP or AZGP1.

The antisense sequences may be modified at a base moiety, sugar moiety or phosphate backbone to improve, e.g., the stability, hybridization, or solubility of the molecule. For example, in the case of nucleotide sequences, phosphodiester linkages may be replaced by thioester linkages making the resulting molecules more resistant to nuclease degradation. Alternatively, the deoxyribose phosphate backbone of the nucleic acid molecules can be modified to generate peptide nucleic acids (see Hyrup et al. (1996), *Bioorg. Med. Chem.,*

4(1): 5-23). Peptidyl nucleic acids have been shown to hybridize specifically to DNA and RNA under conditions of low ionic strength. Furthermore, it is appreciated that the peptidyl nucleic acid sequences, unlike regular nucleic acid sequences, are not susceptible to nuclease degradation and, therefore, are likely to have greater longevity in vivo. Furthermore, it has been found that peptidyl nucleic acid sequences bind complementary single stranded DNA and RNA strands more strongly than corresponding DNA sequences (PCT/EP92/20702). Similarly, oligoribonucleotide sequences generally are more susceptible to enzymatic attack by ribonucleases than are deoxyribonucleotide sequences, such that oligodeoxyribonucleotides are likely to have greater longevity than oligoribonucleotides for in vivo use.

Additionally, RNAi can serve as an treatment agent. To the extent RNAi is used, double stranded RNA (dsRNA) having one strand identical (or substantially identical) to the target mRNA sequence (e.g. MET, periostin, or PP1 (such as PP1c, PPP1R9B or PPP1R6) mRNA) is introduced to a cell. The dsRNA is cleaved into small interfering RNAs (siRNAs) in the cell, and the siRNAs interact with the RNA induced silencing complex to degrade the target mRNA, ultimately destroying production of a desired protein (e.g. MET, periostin, or PP1 (such as PP1c, PPP1R9B or PPP1R6)). Alternatively, the siRNA can be introduced directly. RNAi can be used as an antagonist against MET, periostin or PP1 (such as PP1c, PPP1R9B or PPP1R6). RNAi that acts with agonistic activity may also be used as an agonist for PIP or AZGP1.

Furthermore, an aptamer can be used as a treatment agent to inhibit MET, periostin or PP1 (such as PP1c, PPP1R9B or PPP1R6) or agonize PIP or AZGP1. Methods for identifying suitable aptamers, for example, via systemic evolution of ligands by exponential enrichment (SELEX), are known in the art and are described, for example, in Ruckman et al. (1998) *J. Biol. Chem.*, 273: 20556-67 and Costantino et al. (1998), *J. Pharm. Sci.*, 87: 1412-20. Additionally, gene therapy can be used, for example to agonize PIP or AZGP1 or inhibit MET, periostin or PP1 (such as PP1c, PPP1R9B or PPP1R6). For example, genes encoding a protein of interest, such as PIP or AZGP1, are introduced to target cells by electroporation, either in vitro or in vivo.

Nucleic acid treatment agents, such as siRNAs are available in the art. For example, siRNAs that target MET mRNA are available from Sigma-Aldrich, St. Louis, Mo. (Cat No. SASI_Hs01_00133000 to SASI_Hs01_00133009), as well as being described in Jagadeeswaran et al. (2006), *Cancer Res.*, 66(1):352-61, and can be used as MET antagonists. SiRNAs that target periostin mRNA are available from Sigma-Aldrich, St. Louis, Mo. (Cat No. SASI_Hs01_00215117 to SASI_Hs01_00215126) and can be used as periostin antagonists. SiRNAs that target PPP1R9B mRNA are available from Sigma-Aldrich, St. Louis, Mo. (Cat No. SASI_Hs01_00231101 to SASI_Hs01_00231110) and can be used as PPP1R9B antagonists. SiRNAs that target PPP1R6 mRNA are available from Sigma-Aldrich, St. Louis, Mo. (Cat No. SASI_Hs01_00174269 to SASI_Hs01_00174278) and can be used as PPP1R6 antagonists. SiRNAs that target PPP1CA mRNA are available from Sigma-Aldrich, St. Louis, Mo. (Cat No. SASI_Hs01_00016506 to SASI_Hs01_00016515) and can be used as PPP1CA antagonists. SiRNAs that target PPP1CB mRNA are available from Sigma-Aldrich, St. Louis, Mo. (Cat No. SASI_Hs01_00166314 to SASI_Hs01_00166323) and can be used as PPP1CB antagonists. SiRNAs that target PPP1CC mRNA are available from Sigma-Aldrich, St. Louis, Mo. (Cat No. SASI_Hs01_00238355 to SASI_Hs01_00238364) and can be used as PPP1CC antagonists.

3) Exemplary Treatment Agents—Small Molecules

To the extent that a treatment agent is a small molecule that either antagonizes the MET, periostin or PP1 (such as PP1c, PPP1R9B or PPP1R6) genes, or their expression products, or agonizes the AZGP1 or PIP genes, or their expression products, such compounds may be synthesized by any of the known chemical synthesis methodologies known in the art. Many small molecule treatment agents are already known. MET antagonists include, for example, tyrosine kinase inhibitors such as (3Z)-N-(3-Chlorophenyl)-3-((3,5-dimethyl-4-((4-methylpiperazin-1-yl)carbonyl)-1H-pyrrol-2-yl)methylene)-N-methyl-2-oxo-2,3-dihydro-1H-indole-5-sulfonamide (SU11274) (available from Sigma-Aldrich, St. Louis, Mo., Cat. No.: S9820) and 1,3-Dihydro-3-((3,5-dimethyl-1H-pyrrol-2-yl)methylene)-2H-indol-2-one (SU5416) (available from Sigma-Aldrich, St. Louis, Mo., Cat. No.: S8442). PP1 (such as PR1c, PPP1R9B or PPP1R6) antagonists include, for example, protein phosphatase inhibitors such as okadaic acid (available from EMD-Calbiochem, Cat. No.: 495,604) and Calyculin A (available from EMD-calbiochem, Cat No.: 208851). Periostin antagonists include, for example, valsartan (available from Novartis Pharma AG) (see also Iekushi et al. (2007), *Hypertension*, 49:1409-1414). PIP agonists include, for example, stimulators of PIP production such as tamoxifen (available from Sigma-Aldrich, St. Louis, Mo., Cat. No.: T5648) (see also, Dejardin et al. (1991), *J. Mol. Endocrinol.*, 7(2):105-12). AZGP1 agonists include, for example, stimulators of AZGP1 production such as rosiglitazone (available from Cayman Chemicals, Ann Arbor, Mich., Cat. No.: 71740), dexamethasone (available from Sigma-Aldrich, St. Louis, Mo., Cat. No.: D8893) and (RR+FSS)-(±)-4-(2-((2-(3-chlorophenyl)-2-hydroxyethyl)amino)propyl)phenoxyacetate (BRL 37344) (available from Tocris Bioscience, Bristol, UK, Cat. No. 0948) (see also, Bao et al. (2005), *FEBS Lett.*, 579:41-7). In certain embodiments, AZGP1 agonists, such as stimulators of AZGP1 production, do not include a steroid.

II. Combination Therapy

Any one or more of the treatment agents described herein may be combined with any other one or more of the treatment agents described herein. For example, any treatment agent that is an antagonist of an upregulated gene or protein, MET, periostin or PP1 (such as PP1c, PPP1R9B or PPP1R6), may be combined with another antagonist of an upregulated gene or protein. Similarly, any treatment agent that is an agonist of a downregulated gene or protein, PIP or AZGP1, may be combined with another agonist of a downregulated gene. Additionally, antagonists and agonists can be combined.

Additionally, any one or more of the treatment agents described herein may be combined with one or more additional polyp treatment modalities. The treatment agent(s) may be administered in any order as well as before, during, or after the additional treatment modality or modalities. The additional treatment modalities, include, treatment with antibiotics, such as with repeated courses and systemic administration, treatment with steroids, either systemically or intranasally, treatment with allergy shots (i.e., immunotherapy), such as with a series of injections (shots), or a surgical procedure to reduce the size of or remove a polyp.

III. Treatment Agent Administration and Dosing

The type and amount of treatment agent to be administered will depend upon the particular polyp to be treated or on the particular symptom or type of sinusitis or asthma to be treated. It is contemplated, however, that optimal treatment agents, modes of administration and dosages may be determined empirically. The treatment agent may be administered in a pharmaceutically acceptable carrier or vehicle so that administration does not otherwise adversely affect the recipient's electrolyte and/or volume balance.

Small molecule treatment agents may be administered at doses ranging, for example, from 1-1500 mg/m$^2$, for example, about 3, 30, 60, 90, 180, 300, 600, 900, 1200 or 1500 mg/m$^2$. Protein, peptide or nucleic acid based treatment agents can be administered at doses ranging, for example, from about 0.001 to about 500 mg/kg, more preferably from about 0.01 to about 250 mg/kg, and most preferably from about 0.1 to about 100 mg/kg. The treatment agents may be administered in any one of a wide variety of routes, for example, by a topical, transdermal, nasal, otic, intraperitoneal, intracranial, intracerebroventricular, intracerebral, intravaginal, intrauterine, oral, rectal, or parenteral (e.g., intravenous, intralymphatic, intraspinal, subcutaneous or intramuscular) route.

Pharmaceutical compositions for topical administration of the treatment agents are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent); it is also desirable in some embodiments for this phase to further comprise a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, stabilizers, etc.

Formulations suitable for nasal administration of the treatment agents, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, and include aqueous or oily solutions of the agents. Formulations suitable for otic administration of the treatment agents include drops containing such agents and topical formulations.

Compositions of the present invention can include a liquid carrier. As used herein, the phrases "liquid carrier" or "liquid nasal carrier" refer to a liquid vehicle (e.g., solution, emulsion, or suspension) designed for delivery of a drug to the nasal mucosa of a subject. The liquid nasal carrier can include one or more excipients such as diluents, solvents and/or co-solvents suitable for application to the area of application, such as the nasal mucosa. Suitable diluents include aqueous or non-aqueous diluents or combination thereof. Examples of aqueous diluents include, but are not limited to, saline, water, water for injection (WFI), dextrose or combinations thereof.

In one embodiment, the liquid nasal carrier comprises a solvent such as a water miscible solvent. Non-limiting examples of suitable solvents include propylene glycol, alcohol, glycerol, isopropyl alcohol and polyethylene glycol.

Any desired aqueous and/or non-aqueous diluents, solvents or co-solvents can be added in various concentrations and combinations to form compositions of the invention. The liquid nasal carrier can be present in any suitable amount, for example about 10% to about 99%, about 20% to about 98%, about 30% to about 97%, by weight-in-volume (w/v) of the composition. In another embodiment, the liquid nasal carrier can be added to the other components of the composition in an amount sufficient to q.s. the composition to a desired final volume.

In one embodiment, at least a portion of, at least a therapeutically effective portion of, at least about 20% (w/v), at least about 50% (w/v), at least about 75% (w/v), at least about 90% (w/v), or substantially all of the treatment agent is in dissolved or solubilized form in the liquid carrier.

Compositions of the invention optionally comprise one or more additional pharmaceutically acceptable excipients. The term "excipient" herein means any substance, not itself a treatment agent, used as a carrier or vehicle for delivery of a treatment agent to a subject or added to a pharmaceutical composition to improve its handling or storage properties or to permit or facilitate formation of a unit dose formulation of the composition.

Illustrative excipients include antioxidants, surfactants, adhesives, agents to adjust the pH and osmolarity, preservatives, antioxidants, thickening agents, sweetening agents, flavoring agents, taste masking agents, colorants, buffering agents, and penetration enhancers. Generally speaking, a given excipient, if present, will be present in an amount of about 0.001% to about 20% (w/v), about 0.01% (w/v) to about 10% (w/v), about 0.02% (w/v) to about 5% (w/v), or about 0.3% (w/v) to about 2.5% (w/v).

Illustrative antioxidants for use in the present invention include, but are not limited to, butylated hydroxytoluene, butylated hydroxyanisole, potassium metabisulfite, and the like. One or more antioxidants, if desired, are typically present in a composition of the invention in an amount of about 0.01% (w/v) to about 2.5% (w/v), for example about 0.01% (w/v), about 0.05% (w/v), about 0.1% (w/v), about 0.5% (w/v), about 1% (w/v), about 1.5% (w/v), about 1.75% (w/v), about 2% (w/v), about 2.25% (w/v), or about 2.5% (w/v).

In various embodiments, compositions of the invention comprise a preservative. Ideally, the optional preservative will be present in quantities sufficient to preserve the composition, but in quantities low enough that they do not cause irritation of the area of application of the treatment agent, such as the nasal mucosa. Suitable preservatives include, but are not limited to, benzalkonium chloride, methyl, ethyl, propyl or butylparaben, benzyl alcohol, phenylethyl alcohol, benzethonium, or combination thereof. Typically, the optional preservative is present in an amount of about 0.01% (w/v) to about 0.5% (w/v) or about 0.01% (w/v) to about 2.5% (w/v).

In other embodiments, compositions of the invention are preservative-free. As used herein, the term "preservative-free" includes compositions that do not contain any preservative. Thus, in various embodiments, the composition does not contain, for example, benzalkonium chloride, methyl, ethyl, propyl or butylparaben, benzyl alcohol, phenylethyl alcohol, or benzethonium.

In one embodiment, compositions of the invention optionally comprise a buffering agent. The optional buffering agent, if present, is present in a composition of the invention in an amount that does not irritate the area of application of the treatment agent, such as the nasal mucosa. Buffering agents include agents that reduce pH changes. Illustrative classes of buffering agents for use in various embodiments of the present invention comprise a salt of a Group IA metal including, for example, a bicarbonate salt of a Group IA metal, a carbonate salt of a Group IA metal, an alkaline earth metal buffering agent, an aluminum buffering agent, a calcium buffering agent, a sodium buffering agent, or a magnesium buffering agent. Other suitable classes of buffering agents include alkali (sodium and potassium) or alkaline earth (calcium and magnesium) carbonates, phosphates, bicarbonates, citrates, borates, acetates, phthalates, tartrates, succinates and the like, such as sodium or potassium phosphate, citrate, borate, acetate, bicarbonate and carbonate.

Non-limiting examples of suitable buffering agents include aluminum, magnesium hydroxide, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, and trometamol. (Based in part upon the list provided in The Merck Index, Merck & Co. Rahway, N.J. (2001)). Furthermore, combinations or mixtures of any two or more of the above mentioned buffering agents can be used in the pharmaceutical compositions described herein. One or more buffering agents, if desired, are present in compositions of the invention in an amount of about 0.01% (w/v) to about 5% (w/v) or about 0.01% (w/v) to about 3% (w/v).

In one embodiment, compositions of the invention optionally comprise one or more surfactants. Optional surfactants are typically present in a composition of the invention in an amount of about 0.1 mg/mL to about 10 mg/mL, about 0.5 mg/mL to about 5 mg/mL or about 1 mg/mL.

In various embodiments, compositions the invention may include one or more agents that increase viscosity. Illustrative agents that increase viscosity include, but are not limited to, methylcellulose, carboxymethylcellulose sodium, ethylcellulose, carrageenan, carbopol, and/or combinations thereof. Typically, one or more viscosity increasing agents, if desired, are present in compositions of the invention in an amount of about 0.1% (w/v) to about 10% (w/v), or about 0.1% (w/v) to about 5% (w/v).

In various embodiments, compositions of the invention comprise one or more sweeteners and/or flavoring agents. Suitable sweeteners and/or flavoring agents include any agent that sweetens or provides flavor to a pharmaceutical composition. The sweetener or flavoring agent will help mask any bitter or bad taste that may occur if the pharmaceutical composition drips back into the mouth after intranasal administration or is ingested orally during oral administration. By addition of a sweetener or flavoring agent to the pharmaceutical composition, a barrier that a patient may have to taking the pharmaceutical composition because of unpleasant taste can be reduced. Optional sweetening agents and/or flavoring agents are typically present in a composition of the invention in an amount of about 0.1 mg/mL to about 10 mg/mL, about 0.5 mg/mL to about 5 mg/ml or about 1 mg/mL.

Illustrative sweeteners or flavoring agents include, without limitation, acacia syrup, anethole, anise oil, aromatic elixir, benzaldehyde, benzaldehyde elixir, cyclodextrins, caraway, caraway oil, cardamom oil, cardamom seed, cardamom spirit compound, cardamom tincture compound, cherry juice, cherry syrup, cinnamon, cinnamon oil, cinnamon water, citric acid, citric acid syrup, clove oil, cocoa, cocoa syrup, coriander oil, dextrose, eriodictyon, eriodictyon fluidextract, eriodictyon syrup, aromatic, ethylacetate, ethyl vanillin, fennel oil, ginger, ginger fluidextract, ginger oleoresin, dextrose, glucose, sugar, maltodextrin, glycerin, glycyrrhiza, glycyrrhiza elixir, glycyrrhiza extract, glycyrrhiza extract pure, glycyrrhiza fluidextract, glycyrrhiza syrup, honey, isoalcoholic elixir, lavender oil, lemon oil, lemon tincture, mannitol, methyl salicylate, nutmeg oil, orange bitter, elixir, orange bitter, oil, orange flower oil, orange flower water, orange oil, orange peel, bitter, orange peel sweet, tincture, orange spirit compound, orange syrup, peppermint, peppermint oil, peppermint spirit, peppermint water, phenylethyl alcohol, raspberry juice, raspberry syrup, rosemary oil, rose oil, rose water, stronger, saccharin, saccharin calcium, saccharin sodium, sarsaparilla syrup, sarsaparilla compound, sorbitol solution, spearmint, spearmint oil, sucrose, sucralose, syrup, thyme oil, tolu balsam, tolu balsam syrup, vanilla, vanilla tincture, vanillin, wild cherry syrup, or combinations thereof.

Illustrative taste masking agents include, but are not limited to, cyclodextrins, cyclodextrins emulsions, cyclodextrins particles, cyclodextrins complexes, or combinations thereof.

The foregoing excipients can have multiple roles as is known in the art. For example, some flavoring agents can serve as sweeteners as well as a flavoring agent. Therefore, classification of excipients above is not to be construed as limiting in any manner.

Pharmaceutical compositions as disclosed herein are not limited to any particular pH. In one embodiment, pH of a composition of the invention ranges from about 3 to about 7, about 3 to about 6, or about 4 to about 6, for example about 5. If adjustment of pH is needed, it can be achieved by the addition of an appropriate acid, such as for example, hydrochloric acid, or base, such as for example, sodium hydroxide.

Formulations suitable for administration of treatment agents may include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. The formulations may also be presented in continuous release vehicles. Extemporaneous injection solutions and suspensions may be prepared from sterile powders, granules and tablets of the kind previously described. The excipient formulations may conveniently be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

The treatment agents may be administered in a single bolus, in multiple boluses, or in a continuous release format. Accordingly, formulations may contain a single dose or unit, multiple doses or units, or a dosage for extended delivery of the treatment agents. It should be understood that in addition to the ingredients mentioned above, the formulations of the present invention may include other agents conventional in the art having regard to the type of delivery in question. For example, the carrier may comprise, for example, physiologic saline, or may comprise components necessary for, for example, administration as an ointment, administration via encapsulated microspheres or liposomes, or administration via a device for continuous release.

The treatment agents may be administered systemically or locally. For example, administration may be provided locally as a single or periodic bolus, for example, by parenteral, topical, nasal, or otic administration. For example, the agent can be administered to the sinonasal passages, other respiratory passages, and/or adjacent to a polyp. Administration also may be provided systemically as a single or periodic bolus, for example, intravenously or intralymphatically, or locally as a periodic bolus, for example, by injection, deposition, or as periodic infusion from an internal reservoir or from an external reservoir (for example, from an intravenous bag). The treatment agents may be administered systemically or locally in a continuous release format.

In combination treatments, a treatment agent may be administered to the subject prior to other treatment(s). It may alternatively or additionally be administered during and/or after the other treatment(s). A treatment agent may be used in combination with other treatment modalities of a polyp. For example, a polyp may be treated conventionally with an antibiotic, a steroid, an allergy shot, surgery, or combinations thereof.

The foregoing methods and compositions of the invention are useful in treating a polyp and thereby attenuate growth of the polyp or to regress the polyp, and to treat various of conditions associated with the polyp, including, for example, CRS and ASA. Moreover, the foregoing methods and compositions of the invention are useful in treating sinusitis or asthma and thereby alleviate a symptom of the sinusitis or asthma.

The invention is illustrated further by reference to the following non-limiting example.

EXAMPLE

Example 1

Gene Expression Profiling of Nasal Polyps Associated with Chronic Sinusitis and Aspirin-Sensitive Asthma In this experiment, characteristic transcriptional signatures of chronic rhinosinusitis and aspirin-sensitive asthma were identified through genome-wide transcriptional profiling of nasal polyp tissue. Thirty genome-wide expression microarrays were used to compare nasal polyp tissue from patients with chronic rhinosinusitis alone (n=10) or chronic rhinosinusitis and a history of aspirin-sensitive asthma (n=10) to normal sinonasal mucosa from patients having non-sinus related conditions (n=10). Genes found to be most characteristic of each polyp phenotype, as determined from bioinformatic analyses, were then validated using real-time quantitative PCR and immunohistochemistry in a different set of patients. The experimental data show that transcriptional signature of the control mucosa was distinctly different from that of either polyp phenotype. Genes most characteristic of the CRS phenotype included two upregulated genes—MET and PPP1R9B—and two downregulated genes—PIP and AZGP1. The gene most characteristic of the ASA phenotype was periostin, which was upregulated relative to controls. Differences between the CRS and ASA phenotypes were associated with regional alteration within the 6p22, 22q13 and 1q23 chromosomal regions. Thus, nasal polyps have characteristic transcriptional signatures compared to normal sinonasal mucosa. The five genes identified herein (MET, periostin, PIP, AZGP1, and PP1 (such as PP1c, PPP1R9B or PPP1R6)) play roles in the pathogenesis of polyps, including nasal polyps such as those associated with CRS and ASA, and are therefore targets for therapies for polyps, including nasal polyps. Moreover, given that the five genes were identified in disease-state tissue from those having sinusitis (i.e., chronic rhinosinusitis) and from those having asthma (i.e., chronic rhino sinusitis with aspirin-sensitive asthma), the treatments discussed herein with regard to polyps, such as nasal polyps, such as those associated with chronic sinusitis and aspirin-sensitive asthma, are equally applicable for treating sinusitis or asthma generally, for example by alleviating a symptom of sinusitis or asthma, such as a nasal polyp.

I. Materials and Methods

1) Study Population and Tissue Collection

Sinonasal tissue was collected from 57 patients with distinct phenotypes: (1) patients with chronic rhinosinusitis and sinonasal polyposis without a history of aspirin allergy (CRS group), (2) patients with chronic rhinosinusitis and sinonasal polyposis with a history of asthma and aspirin allergy (ASA group), and (3) patients with no history or clinical evidence of sinusitis, asthma, or aspirin allergy (control group).

Microarray analyses were performed in 30 subjects—10 in each of the 3 phenotypic groups. Results were corroborated with RT-qPCR and immunohistochemistry using tissue from a separate set of subjects (FIG. 5).

All patients underwent nasal endoscopy and sinus computed tomography (CT) to determine the extent and location of their polyps. To ensure a study population of patients with a phenotype for severe sinus disease, enrollment of polyp patients required a CT stage of 3 or higher, indicating bilateral disease with frontal and/or sphenoid involvement, according to a previously described staging system (Gliklich et al. (1994), Am. J. Rhinol., 8(6):291-7). The refractory nature of the polyp disease in study subjects was also reflected by the finding that at least one previous sinus surgery for removal of polyps had been performed in half of the CRS patients and all of the ASA patients (FIG. 5). Exclusion criteria included age less than 18 years, a history of cigarette smoking within one year of surgery, or use of oral steroids within one month of surgery.

Study specimens were obtained under general anesthesia at the start of the patient's surgical procedure. Polyps were harvested from the anterior nasal cavity or ethmoid sinus for patients in the CRS and ASA groups. For control patients, mucosa was obtained from the inferior turbinate (n=3) or ethmoid sinus (n=7) during the performance of non-sinus surgery, including septoplasty (n=4), dacryocystorhinostomy (n=5), and orbital decompression (n=1). All tissue specimens were rinsed in normal saline to remove blood and mucous prior to processing. Tissue collected for microarray and RT-qPCR analysis was immediately placed in RNAlater (Ambion, Austin, Tex., Cat. No.: AM7021) and stored at −80° C. until RNA extraction.

2) RNA Extraction

Total RNA was purified using RNeasy spin-columns (Qiagen) according to the manufacturer's protocol and a modification for hypocellular, dense connective tissues (Reno et al. (1997), Biotechniques 22(6):1082-6), as previously described (Stankovic et al. (2007), Audiol Neurootol 12(5): 334-43). Quantification and quality assessment of the RNA was performed using Agilent 2100 Bioanalyzer and RNA Pico Kit (Agilent Technologies, Santa Clara, Calif.). Only samples that yielded clean and undegraded RNA based on the appearance of electropherograms and RNA integrity numbers greater than 7 were used. The RNA extracted for RT-qPCR met the same quality standards. The RNA was reverse transcribed with Taqman Reverse Transcription Reagents kit (Applied Biosystems, Foster City, Calif.).

3) Microarray Processing and Analysis

Preparation of cRNA, hybridization to the Affymetrix HG-U133 plus 2.0 GeneChip (Affymetrix, Santa Clara, Calif.), and scanning of the chip was performed according to the manufacturer's protocol in a core facility at the Harvard Medical School—Partners Healthcare Center for Genetics and Genomics (Cambridge, Mass.).

Data from microarrays was analyzed using the GenePattern 3.0 platform (GenePattern 3.0, available at: www.broad.mit.edu/genepattern/). Two unsupervised clustering algorithms—self-organizing maps (SOM) (Tamayo et al. (1999), PNAS (USA), 96(6):2907-12) and hierarchical clustering (Eisen et al. (1998), PNAS (USA), 95(25):14863-8)—were used to determine which samples clustered without a priori knowledge of which sample came from which phenotypic group. The stability of the identified clusters was assessed using consensus clustering (Monti et al. (2003), Machine learning, 52:91-118). Class neighbors analysis (Golub et al. (1999), Science, 286(5439):531-7) and comparative marker selection (Gould et al. (2006), Bioinformatics, 22(15):1924-5) were used to determine which genes best characterize a patient group when there was a priori knowledge of which sample came from what group. Genes were ranked using the t-test statistic. The false discovery rate (FDR) statistic was used, and set to <10% to adjust for multiple hypothesis testing while estimating probabilities that differences in gene expression represent false positive findings. The robustness of the genes that best characterize a group was tested using K-nearest neighbors cross validation (Golub et al. (1999), Science, 286(5439):531-7).

Gene Set Enrichment Analysis (GSEA) (Subramanian et al. (2005), PNAS (USA), 102(43):15545-50) was used to determine whether an a prior defined set of genes, including cytogenetic bands, metabolic and signaling pathways, and neighborhoods clustered on cancer-related genes, showed statistically significant and concordant differences between the CRS and ASA groups. Correction for multiple hypotheses testing and gene set size was automatically implemented using sample permutations. Gene sets that contain fewer than 25 genes and more than 500 genes were ignored, which is appropriate for datasets with more than 10,000 features (Subramanian et al. (2005), PNAS (USA), 102(43):15545-50).

4) RT-qPCR Quantification of Relative mRNA

Real-time quantitative PCR was used to validate expression of 5 genes determined to be most characteristic of the groups studied. For these genes, 6-FAM linked fluorescent probes and primers were designed and optimized by Applied Biosystems (Foster City, Calif.). The measurements were carried out on an Applied Biosystems 7700 Sequence Detector using 96 well plates and conditions as previously described (Stankovic et al. (2007), Audiol Neurootol 12(5): 334-43).

5) Immunohistochemistry

Intraoperative specimens were embedded in paraffin and serially sectioned at a thickness of 10 μm. Immunostaining was done as previously described (Adams (1992), J. Histochem. Cytochem., 40(10):1457-63) using primary polyclonal antibodies raised against human Zn-α2-glycoprotein (Santa Cruz Biotechnology, Inc, Santa Cruz, Calif., sc-11238; 1:500 dilution), human hepatocyte growth factor receptor, Met (Santa Cruz Biotechnology, Inc, SC-10; 1:750 dilution), human neurabin 2 (also known as PPP1R9B) (Abcam, Inc, Cambridge, Mass., ab18561; 1:500 dilution), human periostin (BioVendor Laboratory Medicine, Inc., Modrice, Czech Republic, RD-181045050; 1:40,000 dilution) and monoclonal antibodies against human prolactin-induced protein (Signet Laboratories, Cambridge, Mass., 611-01; 1:1,600 dilution). Control slides, which did not stain, were processed in parallel, but not exposed to the primary antibody.

Informed consent was obtained from all subjects according to the study protocol approval by the Human Studies Committee of the Massachusetts Eye and Ear Infirmary.

II. Results

Similarities between patterns of gene expression in the samples studied with microarrays are depicted in the square heat map shown in FIG. 1. Consensus hierarchical clustering was performed assuming three clusters. Bright red colors (generally in the small upper left quadrant and in the large lower right quadrant) indicate samples that always clustered, whereas dark blue colors (generally in the rectangular upper right quadrant and the rectangular lower left quadrant) indicate samples that never clustered. Control samples co-clustered forming the upper red block, whereas CRS and ASA samples intermingled forming the lower red block.

Figure 2:
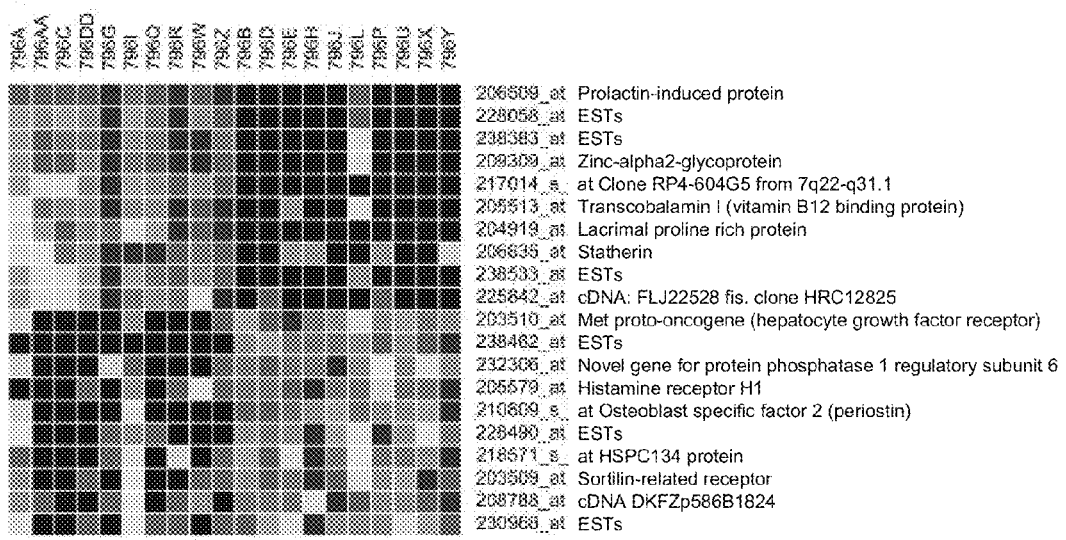
FIGS. 2A and 2B are heat maps of microarray data using class neighbors analysis applied to CRS and control group (FIG. 2A), or ASA and control group (FIG. 2B). Red (primarily in the upper left and lower right quadrants of FIGS. 2A and 2B) indicates high levels of gene expression, and blue (primarily in the upper right and lower left quadrants of FIGS. 2A and 2B) indicates low levels of gene expression. The first 10 columns are control samples (FIGS. 2A and 2B), and the last 10 columns are CRS (FIG. 2A) or ASA samples (FIG. 2B). Horizontal labels indicate Affymetrix feature followed by gene name.
Figure 2:
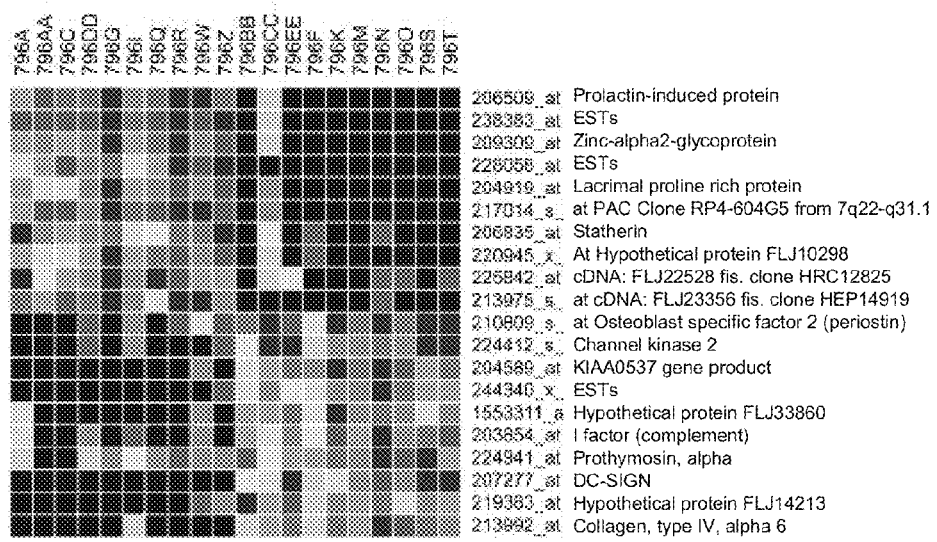

Given how different the CRS and ASA groups were from the control group, it is desirable to define the smallest set of genes that best differentiated the groups. The results are summarized in heat maps (FIG. 2) where columns represent different samples, rows represent gene expressions levels, and color reflects levels of gene expression with red indicating high and blue indicating low levels of expression. For simplicity, only the 20 most characteristic genes and expressed sequence tags (ESTs) are shown in FIG. 2, although 808 genes were expressed at higher levels (i.e., upregulated) in controls and 2724 genes were upregulated in CRS when comparing control and CRS samples, and 468 genes were upregulated in controls and 697 genes were upregulated in ASA when comparing control and ASA samples. FIG. 2 demonstrates high reproducibility of the measurements with samples from the same group having similar color coding.

The genes that best characterize each phenotypic group are known as predictor genes. These genes do not necessarily demonstrate the largest difference in expression between two groups, but rather exhibit a small variance within a group in addition to a substantial difference between groups (Golub et al. (1999), *Science*, 286(5439):531-7). When comparing CRS group with controls, 4 genes were found to be sufficient at each cross validation step to correctly predict 19 out of 20 samples. Out of 80 possible genes across all 20 steps of cross validation, the following 4 genes were used most commonly (69 out of 80 times), and therefore best differentiate the CRS group from controls: PIP, MET, AZGP1 and a sequence from clone RP4-551D2 on chromosome 20q13.2-13.33 that contains a gene for PPP1R6. When comparing the ASA group with controls, 2 genes were sufficient at each cross validation step to correctly predict all 20 samples. Out of 40 possible genes across all 20 steps of cross validation, the following 2 were used most commonly (30 out of 40 times): periostin and EST Hs.226268. The relative levels of expression of these genes are summarized in FIG. 6.

The microarray data were validated using RT-qPCR. Results are summarized in FIG. 6 and in FIG. 3 where expression of the 5 most characteristic genes is plotted for each patient group relative to the control group. FIG. 6 indicates that the RT-qPCR data were in overall good agreement with the microarray data although the magnitude of the divergence between the groups differed somewhat between the two techniques. PPP1R9B was studied in place of PPP1R6 because the two genes are related, PPP1R9B has been more extensively characterized in the literature, commercially available primers for PPP1R9B exist, and PPP1R6 is only one of the genes within the sequence that also contains a novel cadherin-like protein VR20 gene and the 5' end of the SYCP2 gene for synaptonemal complex protein 2.

The genes most characteristic of CRS (PIP, MET, AZGP1 and PPP1R9B) and ASA (periostin) were all confirmed by RT-qPCR to be expressed at significantly different levels (p<0.05) compared to controls. Furthermore, three of these genes were found to be expressed at significantly different levels between the CRS and ASA group when assessed with RT-qPCR: periostin (p=0.01), MET (p=0.01) and PPP1R9B (p=0.02). However, when comparing the two polyp groups based on microarray data, no single gene had a significant difference in expression between the CRS and ASA even if allowing false detection rate of 50%. This finding is consistent with the results in FIG. 1 where CRS and ASA samples do not segregate into distinct groups. Therefore, GSEA was used to test for sets of related genes that might be systematically altered between the two groups. Three gene sets within distinct chromosomal bands were found to be different between the ASA and CRS groups: 6p22 (FDR=18%; 39 genes in the set), 22q13 (FDR=20%; 65 genes in the set) and 1q23 (FDR=24%; 44 genes in the set). These chromosomal bands do not include the genes studied in FIG. 3, suggesting that there are additional genes that differentiate CRS and ASA groups.

Figure 3:
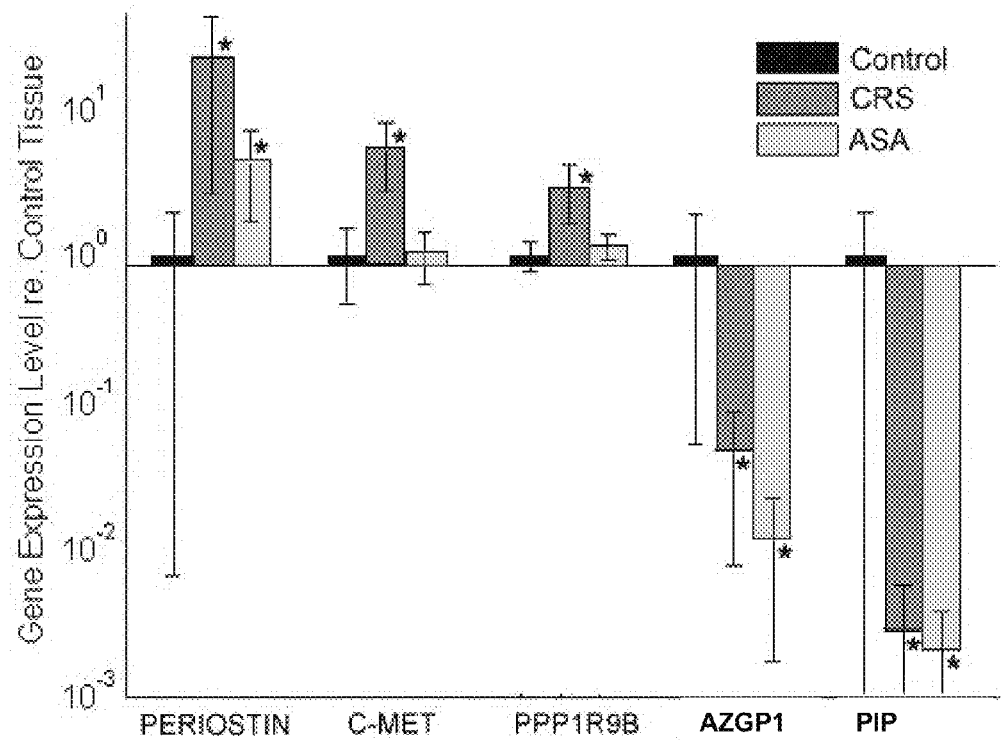
FIG. 3 shows the normalized expression levels of select genes in sinonasal tissue relative to controls. Error bars indicate standard error of the mean. Asterisks indicate statistically significant differences in CRS and ASA groups relative to control. For simplicity, the expression of all five genes was set to one in control tissues, although the relative expression of these genes in decreasing abundance was prolactin-induced protein (PIP): periostin: zinc-alpha2 glycoprotein (AZGP1)
Figure 4:
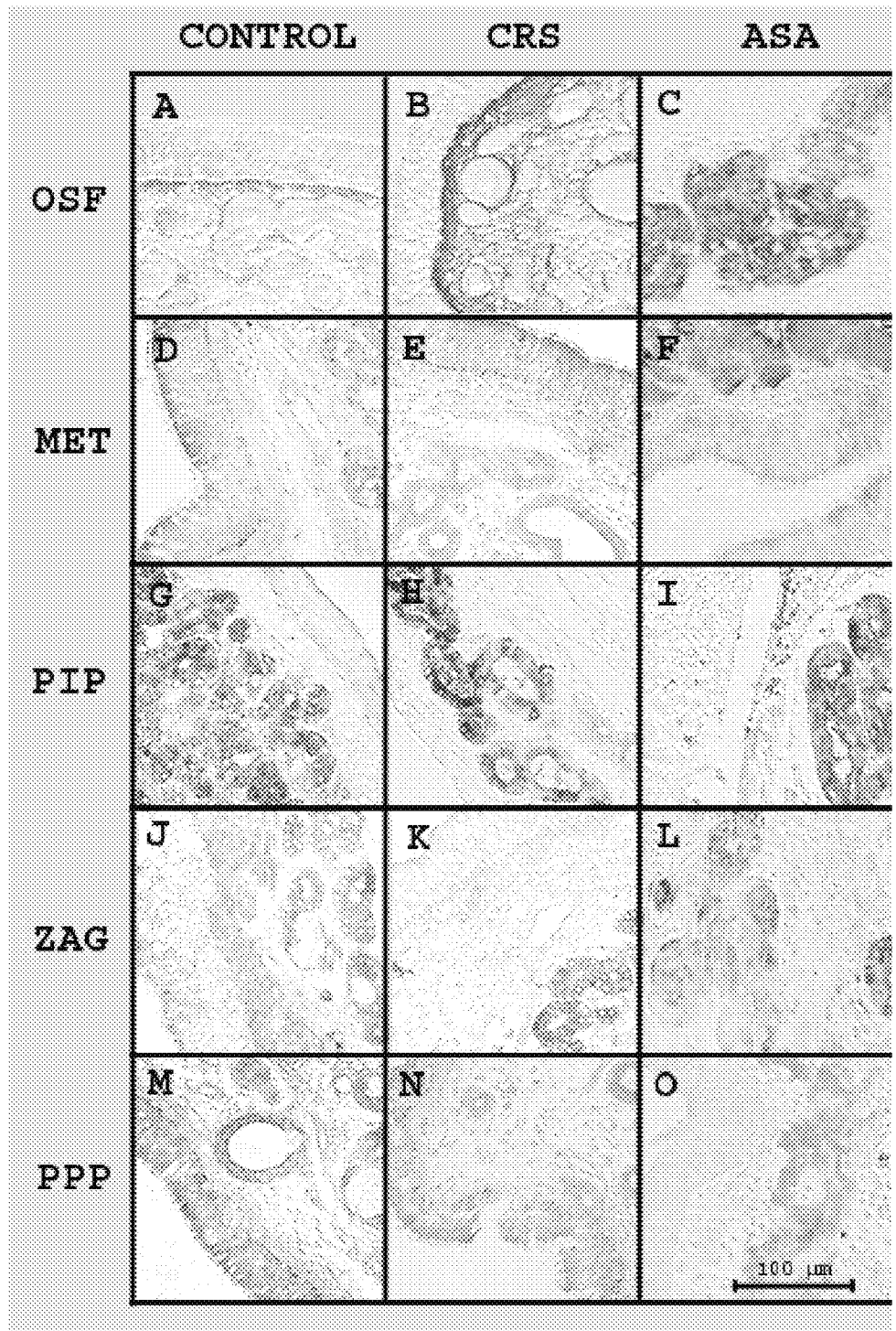

Immunohistochemistry was used to verify microarray data at the protein level, and to determine cellular localization of the gene products of interest. Typical results are summarized in FIG. 4, and they are generally consistent with RT-qPCR data (FIG. 3). In particular, expression of periostin was high in the basolateral surfaces of the glandular and respiratory epithelium of all tissues studied, but did not stain the apical mucosal border (FIGS. 4A-C). The CRS and ASA tissue (FIGS. 4B and C) stained substantially more than the control tissue when the same staining conditions were used. Expression of MET was seen in the glandular cytoplasm and respiratory epithelium of the CRS (FIG. 4E) and control tissues (FIG. 4D), and less in the ASA group (FIG. 4F). PIP showed more expression at the epithelial surface in the control tissue (FIG. 4G) than the CRS (FIG. 4H) or ASA (FIG. 4I) tissue, and consistently stained glandular cytoplasm in all groups. The ASA group in particular typically had minimal or no staining of the respiratory epithelium. Expression of AZGP1 was higher in the glandular cytoplasm than the respiratory epithelium of all groups (FIGS. 4J-L). Expression of PPP1R9B was similar in all groups, with staining of the glandular and mucosal epithelium (FIGS. 4M-O).

III. Discussion

Although several reports have described the use of microarray technology to examine sinonasal tissues, this study is believed to be the first to screen the entire human genome for alterations in gene expression in nasal polyps from patients with sinusitis and asthma. In an attempt to elucidate those genes with greatest impact, the current study screened patients for distinct phenotypes (CRS and ASA), performed bioinformatic analyses on highly reproducible microarray data, and validated select genes with two complementary techniques (RT-qPCR and immunohistochemistry) applied to different patient sets. Five genes were identified for their strong association with these disease entities—periostin, MET, AZGP1, PIP, and PPP1R9B.

Periostin, which has not been previously described in sinonasal tissue, was found to be abundantly expressed in normal mucosa and markedly elevated in polyps from both CRS and ASA patients, suggesting that it plays a role in the normal physiology and pathophysiology of sinonasal mucosa. Periostin is known to be a potent regulator of fibrosis and collagen deposition (Norris et al. (2007), *J. Cell. Bio-*

*chem.*, 101(3):695-711). Its overexpression may be a primary contributor to pathogenesis of sinonasal polyposis by analogy to myocardial tissue where early activation of periostin and resultant fibrosis is thought to be a primary contributor to cardiac dysfunction, not an advanced secondary phenomenon (Kim et al. (2007), *Science,* 316(5830):1481-4).

A second gene found to be overexpressed in CRS polyps is MET, which encodes a receptor tyrosine kinase that plays an important role in various cellular functions, including increased cell growth, reduced apoptosis, altered cytoskeletal function, increased metastasis, and angiogenesis (Sattler et al. (2007), *Curr. Oncol. Rep.,* 9(2):102-8). These results confirm the findings that reported an over expression of Met and its ligand, hepatocyte growth factor (HGF), in nasal polyps from patients with sinusitis without asthma or aspirin sensitivity (Rho et al. (2006), *Arch. Otolaryngol. Head Neck. Surg.,* 132(9):985-9).

Although periostin and MET were found to be overexpressed in nasal polyps, the expression of PIP, a protein secreted by various apocrine glands, was found to be markedly reduced in both CRS and ASA samples compared to controls. This secretory marker of apocrine differentiation in breast carcinoma (Haagensen et al. (1990), *Ann. N. E Acad. Sci.,* 586:161-173) has also been implicated in host defense against infections and tumors (Bahram et al. (1994), *Proc Natl Acad Sci USA* 91: 6259-6263). The current study results stand in contrast with those of Liu et al. (Liu et al. (2004), *J. Allergy Clin. Immunol.,* 114(4):783-90) who reported over expression of PIP in microarray analysis of nasal polyps from 10 patients, two of whom had ASA. Three additional genes identified by Liu as being upregulated in polyps-statherin, lactoferrin, and DMBP1—were found to be downregulated in both CRS and ASA polyps in the current study, and did not emerge as key predictors of CRS or ASA.

Moreover, uteroglobin was identified as being downregulated in polyps studied by Liu whereas the current study found no statistically significant difference in expression of this gene in either CRS or ASA polyps compared to controls. A possible explanation for these discrepancies is that all of the subjects studied by Liu received intranasal steroids for one month or more prior to surgery, which may have influenced expression levels. Furthermore, two of the four control samples in their study were obtained from the ethmoid sinus in patients who underwent surgery for drainage of maxillary mucoceles. It is possible that the presence of active maxillary sinus disease in these patients could have affected gene expression in the adjacent ethmoid regions. Thus, the present study is considered to be a more valid identification of genes involved with polyps, sinusitis, and asthma.

Another characteristic gene found to be underexpressed in nasal polyps is AZGP1, a member of a distinct, heterogeneous lineage of major histocompatibility complex class I genes. These genes are implicated in a variety of diverse and important physiological functions, including anti-infectious and tumor immunity (Bahram et al. (1994), *PNAS* (USA), 91:6259-63). The mechanism of AZGP1's role in the immune system is thought to be through the binding and presentation of a lipidic entity to T cells (Rolli et al. (2007), *FEBS Lett.,* 581(3):394-400). AZGP1 inhibits cell-cycle dependant proliferation, possibly by downregulating cdc2 cyclin dependant kinase (He et al. (2001), *J. Cell Biochem.,* 81:162-9), whose increased expression has been directly linked to increased proliferation and decreased differentiation of advanced tumors. High levels of AZGP1 expression in the normal nasal mucosa and markedly decreased expression in nasal polyps in the present study is consistent with the idea that underexpression of AZGP1 contributes to cellular proliferation characteristic of polyps.

The final marker gene identified in this study was PPP1R9B, a ubiquitously expressed gene that plays a role in cell growth (Sarrouilhe et al. (2006), *Biochimie,* 88(9):1099-1113) and molecular scaffolding (Satoh et al. (1998), *J. Biol. Chem.,* 243:3470-5) by binding the catalytic subunit of protein phosphatase 1. Although this marker was found at a relatively low baseline level in normal mucosa compared to the other four identified marker genes, a significant increase in expression in CRS polyps was observed. Other regulatory subunits of the protein phosphatase 1 catalytic unit may also contribute to the pathophysiology of sinonasal polyposis.

Other microarray studies of smaller patient populations have reported a variety of genes with altered expression in sinonasal polyps. Fritz et al. reported that mammaglobin, a protein of unknown function found in breast cancer cell lines, was overexpressed in the polyps of three patients with allergic rhinitis compared to controls (Fritz et al. (2003), *J. Allergy Clin. Immunol.,* 112(6):1057-63). Although altered expression of mammaglobin did not emerge as a key predictor of ASA or CRS polyps in the current study, a statistically significant increase in expression of mammaglobin 1 was found in CRS, but not ASA patients, compared to controls. There were no statistically significant changes in mammaglobin 2 in CRS or ASA polyps compared to controls. Benson et al. observed the increased expression of uteroglobin, a presumed anti-inflammatory gene, in polyp tissue in four patients who underwent a six-week course of topical steroid therapy (Benson et al. (2004), *J. Allergy Clin. Immunol.,* 113(6):1137-43) whereas the current study found no alteration in this gene in the polyps compared to controls. In a microarray study of immune-associated genes, Wang et al. found increased expression of IL-17 and its receptor in polyp tissue from four patients with chronic rhinosinusitis compared to controls (Wang et al. (2006), *Ann. Otol. Rhinol. Laryngol.,* 115(6): 450-6). In the current study, there was no statistically significant difference in expression of IL-17 in CRS or ASA polyps compared to controls. Figueiredo et al. studied 96 inflammatory genes in a pooled microarray analysis in patients with non-allergic nasal polyps and found alterations in TGF-B1 and IL-5 compared to controls (Figueiredo et al. (2007), *Am. J. Phinol.,* 21(2):231-5). The current study found no alterations in these two genes. In a study of polyp tissue from three patients with allergic fungal sinusitis and four with eosinophilic mucin rhinosinusitis, Orlandi et al. found four genes—cathepsin B, sialyltransferase 1, GM2 ganglioside activator protein, and S100 calcium binding protein—that were differentially expressed compared to human referenced RNA controls (Orlandi et al. (2007), *Otolaryngol. Head Neck Surg.,* 136(5):707-13). When studying nonallergic chronic rhinosinusitis without polyposis in 14 patients, Anand et al. found four genes associated with inflammatory pathways—TNF-α, IL-6, IL-12A, and IL-13—that were consistently overexpressed in the diseased tissue compared to controls (Anand et al. (2006), *Am J Rhinol* 20(4):471-476).

The inconsistent results reported in these previous studies reflect heterogeneity of the studied populations and inherent difficulties in performing microarray analyses. The challenge to obtain meaningful results from the large volume of data generated by a relatively small patient population demands rigorous bioinformatic analyses and validation. In the present study, only patients with a demonstrated severe phenotype for either of two sinusitis subsets—CRS and ASA—were enrolled. High throughput technology was used that allowed for expression survey of the entire human genome. Validation of the microarray results was performed on an independent set of patients using two complementary techniques to confirm altered expression of the identified genes and localize their protein products in sinonasal tissues. Application of these methods led to the identification of several genes that play a role in the pathogenesis of sinonasal polyposis and are therefore natural targets for therapeutic interventions. Moreover, the considered methodology of the present study is believed to be a more valid identification of genes involved with polyps, sinusitis, and asthma.

Based on the role periostin plays in cell growth, proliferation, motility and migration, a monoclonal antibody directed against periostin has been proposed as an adjunct to chemotherapy for colorectal cancer (Tai et al. (2005), Carcinogenesis, 26(5):908-15). The results of the current study suggest that topically or systemically applied agents against periostin, including anti-periostin monoclonal antibody, can treat patients with polyps, such as those with sinonasal polyposis. This therapeutic scenario is particularly interesting given that polyps often respond partially and transiently to steroid treatment, and that periostin plays a role in subepithelial fibrosis seen in early stages of bronchial asthma (Takayama et al. (2006), J. Allergy Clin. Immunol., 118(1):98-104) that resists steroid treatment.

Many strategies for interfering with the HGF/Met pathway are currently being investigated (Sattler et al. (2007), Curr. Oncol. Rep., 9(2):102-8) because MET is overexpressed and mutated in a variety of malignancies. The results of the current study suggest that MET-dependent polyps associated with CRS, but not ASA, as well as other types of MET-dependent polyps would be expected to respond to inhibition of the HGF/Met pathway.

Pharmacologic treatments aimed at increasing AZGP1 production in polyps can be therapeutic, similar to AZGP1's role in reducing tumor cell proliferation when added to the culture medium as a protein, or transfected as cDNA (He et al. (2001), J. Cell Biochem., 81:162-9). Dexamethasone, a steroid used to treat nasal polyps, stimulates AZGP1 protein production in other tissues (Bing et al. (2004), Proc Natl Acad Sci USA 101(8):2500-5). The use of AZGP1 knockout mice (Rolli et al. (2007), FEBS Lett., 581(3):394-400) may prove useful in confirming therapeutic strategies.

The application of these therapies to the treatment of patients with asthma, as well as sinusitis, is consistent with the unified airway theory (Krouse et al. (2007), Otolaryngol. Head Neck Surg., 136(5):699-706). Common genetic and environmental factors are thought to have similar affects on both the upper and lower airways. As many as one-third of patients diagnosed with sinusitis also present with symptoms of asthma (Bresciani et al. (2001), J Allergy Clin Immunol. 107(1):73-80). In this study, the ASA cohort manifest symptoms of both disease entities, as well as a history of aspirin allergy. Microarray technology has been used to identify alteration in gene expression in patients with asthma, although not in patients with ASA specifically (Gujardo et al. (2005), J. Allergy Clin. Immunol., 115(2):243-51; Yuyama et al. (2002), Cytokine 19(6):287-296).

In this study, the GSEA allowed the association of chromosomal bands on 6p22, 22q13 and 1q23 with the CRS versus ASA phenotype, suggesting that regional alterations with these bands, including chromosomal deletions or amplifications, dosage compensation and epigenetic silencing, contribute to the difference between the phenotypes. It is interesting that two of these chromosomal bands have been associated with asthma. Chromosome 6p has been identified as a susceptibility gene for asthma and allergy (Ober (2005), Immunol. Allergy Clin. North Am., 25(4):669-79) whereas chromosome 22 is associated with susceptibility for asthma and atopy (Koppelman (2001), "In Genetics of Asthma and Atopy," Ph.D. Dissertation, Univ. Of Groningen). Chromosome 1p, but not 1q, has been associated with the development of asthma in patients with environmental exposure to tobacco smoke (Colilla et al. (2003), J. Allergy Clin. Immunol., 111(4):840-6). The fact that none of the 5 genes identified in the current study localized to the three chromosomal bands suggests that those genes likely play more direct roles in the pathogenesis of sinonasal polyposis rather than asthma.

IV. Conclusion

Sinonasal disease is a problem of major clinical and societal impact for which curative therapeutic modalities are often lacking, and molecular pathogenesis remains elusive. The use of high throughput microarray technology validated by RT-qPCR and immunohistochemistry has led to the identification of 5 genes (periostin, MET, AZGP1, PIP and PP1 (such as PP1c, PPP1R6 or PPP1R9B)) that play roles in pathogenesis of sinonasal polyps associated with CRS and ASA. These genes may serve as therapeutic targets for medical management of patients with chronic sinusitis and asthma. More broadly, these findings indicate that the 5 genes, and the proteins they encode, are targets for treating polyps, such as nasal polyps. Insofar as the MET, periostin and PP1 (such as PPP1R9B and PPP1R6) genes are upregulated (or are otherwise associated with a gene that is upregulated, such as PP1c) in those with polyps, therapies which inhibit the transcription of these genes, the expression of the proteins encoded by these genes, or the activity of the proteins encoded by these genes or the biological regulatory systems (upstream and downstream) to which they belong (i.e., downregulate the transcription, expression, or activity of the targets) are useful. Similarly, as the AZGP1 and PIP genes are downregulated in those with polyps, therapies which add exogenous proteins encoded by these genes, or increase the transcription of these genes, the expression of the proteins encoded by these genes, or the activity of the proteins encoded by these genes or the biological regulatory systems (upstream and downstream) to which they belong (i.e., upregulate the amount, transcription, expression, or activity of the targets), are useful. Moreover, given that the five genes were identified in disease-state tissue from those having sinusitis (i.e., chronic rhinosinusitis) and from those having asthma (i.e., chronic rhinosinusitis with aspirin-sensitive asthma), the treatments discussed herein with regard to polyps, such as nasal polyps, such as those associated with chronic sinusitis and aspirin-sensitive asthma, are equally applicable for treating sinusitis or asthma generally, for example by alleviating a symptom of sinusitis or asthma, such as a nasal polyp.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

The entire disclosure of each of the patent documents, scientific publications, and other gene and protein database references disclosed hereinabove is expressly incorporated herein by reference for all purposes.

What is claimed is:

1. A method for downregulating periostin in polyp tissue, the method comprising delivering an antagonist of periostin to the polyp tissue in an amount sufficient to downregulate periostin in the polyp tissue.

2. The method of claim 1, wherein the antagonist of periostin is selected from the group consisting of an anti-periostin antibody, valsartan, and a small interfering RNA.

3. The method of claim 1, wherein the antagonist of periostin is valsartan.

4. A method for treating a polyp, the method comprising administering to a subject having or suspected of developing a polyp an antagonist of periostin in an amount sufficient to attenuate growth of the polyp or to regress the polyp.

5. The method of claim 4, wherein the polyp comprises a nasal polyp.

6. The method of claim 4, wherein the subject has a disorder selected from the group consisting of sinusitis, chronic rhinosinusitis, asthma, and aspirin-sensitive asthma.

7. The method of claim 4, wherein the agent is administered locally or systemically.

8. The method of claim 4, wherein the antagonist of periostin is selected from the group consisting of an anti-periostin antibody, valsartan, and a small interfering RNA.

9. The method of claim 4, wherein the antagonist of periostin is valsartan.

10. A method for treating sinusitis or asthma, the method comprising administering to a subject having or suspected of developing sinusitis an antagonist of periostin in an amount sufficient to alleviate a symptom of the sinusitis or asthma.

11. The method of claim 10, wherein the symptom comprises a nasal polyp.

12. The method of claim 10, wherein the subject has chronic rhinosinusitis or aspirin-sensitive asthma.

13. The method of claim 10, wherein the antagonist of periostin is selected from the group consisting of an anti-periostin antibody, valsartan, and a small interfering RNA.

14. The method of claim 10, wherein the antagonist of periostin is valsartan.

* * * * *